US007179886B1

(12) United States Patent
Feighner et al.

(10) Patent No.: US 7,179,886 B1
(45) Date of Patent: Feb. 20, 2007

(54) CLONING AND IDENTIFICATION OF THE MOTILIN RECEPTOR

(75) Inventors: Scott D. Feighner, Holmdel, NJ (US); Arthur A. Patchett, Westfield, NJ (US); Carina Tan, Metuchen, NJ (US); Karen Kulju McKee, Middletown, NJ (US); Douglas MacNeil, Westfield, NJ (US); Andrew D. Howard, Park Ridge, NJ (US); Sheng-Shung Pong, Edison, NJ (US); Roy G. Smith, Houston, TX (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/719,485

(22) PCT Filed: Jun. 8, 1999

(86) PCT No.: PCT/US99/12773

§ 371 (c)(1), (2), (4) Date: May 25, 2001

(87) PCT Pub. No.: WO99/64436

PCT Pub. Date: Dec. 16, 1999

(51) Int. Cl.
*G01N 33/53* (2006.01)
*C01K 14/00* (2006.01)
*C12P 21/06* (2006.01)

(52) U.S. Cl. ...................... 530/350; 435/7.1; 435/69.1; 435/325; 435/320.1

(58) Field of Classification Search ............... 435/69.1, 435/320.1, 325, 252.3, 172.3, 7.1; 536/23.1, 536/24.31; 530/300, 350
See application file for complete search history.

(56) References Cited

U.S. PATENT DOCUMENTS 5,155,218 A * 10/1992 Weinshank et al. ........ 536/23.5
5,712,253 A 1/1998 Lartey et al.

FOREIGN PATENT DOCUMENTS

WO WO 01/32710 5/2001

OTHER PUBLICATIONS

Harigaya et al, Generation of functional clonal cell lines from human bone marrow stroma, Proc. Natl. Acad. Sci. USA, vol. 82, pp. 3477-3480, May 1985.*

Depoortere, I et al. "Motilin Receptors of the Rabbit Colon", PEPTIDES, (1991), vol. 12, pp. 89-94.

Depoortere, I et al. "Distribution and Characterization of Motilin Receptors in the Cat", PEPTIDES, (1993), vol. 14, pp. 1153-1157.

De Clercq, P. et al. "Isolation, Sequence, and Bioactivity of Chicken Motilin", PEPTIDES, (1996), vol. 17, No. 2, pp. 203-208.

Poitras, P. et al. "Heterogeneity of Motilin Receptors in the Gastrointestinal Tract of the Rabbit", (1996), vol. 17, No. 4, pp. 701-707.

Depoortere, I. et al. "Identification of Motilin mRNA in the Brain of Man and Rabbit. Conservation of Polymorphism of the Motilin Gene across Species". PEPTIDES, (1997), vol. 18, No. 10, pp. 1497-1503.

Coulie, Bernard et al. "Identification of Peptide Ligand-binding Domains within the Human Motilin Receptor Uising Photoaffinity Labeling". The Journal of Biological Chemistry, (2001), vol. 276, No. 38, pp. 35518-35522.

Smith, Roy G. et al., "Growth Hormone Releasing Substances: Types and Their Receptors". Hormone Research, (1999), vol. 51, pp. 1-8.

McKee, Karen Kulju et al., "Cloning and Characterization of Two Human G Protein-Coupled Receptor Genes (GPR38 and GPR39) Related to the Growth Hormone Secretagogue and Neurotensin Receptors", Genomics, Dec. 1997, vol. 46, pp. 426-434.

Palyha, Oksana C. et al., 1998, Database GEN EMBL Submission, Accession No. AF082210.

Feighner, Scott D. et al., "Receptor for Motilin Identified in the Human Gastrointestinal System", Science, Jun. 1999, vol. 284, pp. 2184-2188.

* cited by examiner

*Primary Examiner*—Gary B. Nickol
*Assistant Examiner*—Nirmal S. Basi
(74) *Attorney, Agent, or Firm*—Jack L Tribble; Patricia L Chisholm

(57) ABSTRACT

The motilin receptor has been isolated and cloned, and nucleic acid sequences are given. Two spice variants have been identified. Also, assays for motilin receptor ligands are given. The identification of the cloned motilin receptor may be used to screen and identify compounds which bind to the receptor for use in a variety of gastric conditions, including gastric motility disorders.

5 Claims, 13 Drawing Sheets

TTGAAATTATCTGGTCACTGCCGGGCGCGGTGGCTCACGCCTGTAATCCCAGCACTTTGGGAGGTCGA
GGCGGGTGGACCACCTGGGGTCAGGAGTTCGAGACCAGGCTGGCCAACATGGCGAAACCCTGACTACA
CAAAAAACACAAAATTTAGCCGGGGCTTGGGCGCTCCTGTGCTCCCAGCTACTCAGGAGGCTGAGGTG
GGAGGACTGCTTGAGCCTGGGAGGTCGAGGCTGCAGTGAGCTGTGATCGCGCCACTTAAACTCCAGCC
TGGACGACAGTGAGACCCTGTCTCAAGAAGAAAAAAAGAAAGAAAGAAAGAAAAAAAGAAAAAAAAGA
AATTATTTGGTCAATTATATGGTCAGCTCCCTCCACCACTCGCGAATTTACAGAAGAGGAGAACTGGG
CTGGGCGAGACCAGGACTAGCCCAAGATTACACAAGTTACTCGGTTGTAGAGCCAGGATTAGACAGGA
GAGGCTCTAGATTCTGGTCTAGACTCCCCTCCTATTATTTAGCATTATGGCTTCCTGAGGATTACCAT
GAGCCCTCCTCCACCGTCAAGCGGCAGCTACCAGCCACCAGACCAGATCCCTTCGAAGGTGCCCGGAG
TACCAGACTGACAAAAGCGCCCGTACAGTGCTCAGTCCTGTAACCAAAGCTGTCTAGGGTGCAGACAT
CGCTCACCGGACCGGGTAGGGCTCGTGCGCTAAGGGCGCCGGGTATTCCAGTTAGTGGAGAGGGAAGC
GCCCTGGAACTGCATGGCCCGGGAGAGGGCGCGGGAGCGGAGCATGGCCGGGCCGGGGCGGGCCGCG
GCCGTGGGCGGAGACTGCGCGCAGCTAGCTCGGGAGCGCCTCGGAGCC QCCCCGCAGAGCCGCTTCT
CGCGCCCCGCAGCGCAGCGCAGCGCTCCGCCGTCTGACCTGCCGCGCCCGCAGCGTGCGGGCTGGGAA
AGGAGGCGCTCACCGAGAGGGACCACGCGCCAGGCTCCCAGCCCGACCCGGGACGCGGCGGCCGCGCG
GAGCACCCATGGGCAGCCCCTGGAACGGCAGCGACGGCCCCGAGGGGGCGCGGGAGCCGCCGTGGCCC
GCGCTGCCGCCTTGCGACGAGCGCCGCTGCTCGCCCTTTCCCCTGGGGGCGCTGGTGCCGGTGACCGC
TGTGTGCCTGTGCCTGTTCGTCGTCGGGGTGAGCGGCAACGTGGTGACCGTGATGCTGATCGGGCGCT
ACCGGGACATGCGGACCACCACCAACTTGTACCTGGGCAGCATGGCCGTGTCCGACCTACTCATCCTG
CTCGGGCTGCCGTTCGACCTGTACCGCCTCTGGCGCTCGCGGCCCTGGGTGTTCGGGCCGCTGCTCTG
CCGCCTGTCCCTCTACGTGGGCGAGGGCTGCACCTACGCCACGCTGCTGCACATGACCGCGCTCAGCG
TCGAGCGCTACCTGGCCATCTGCCGCCCGCTCCGCGCCCGCGTCTTGGTCACCCGGCGCCGCGTCCGC
GCGCTCATCGCTGTGCTCTGGGCCGTGGCGCTGCTCTCTGCCGGTCCCTTCTTGTTCCTGGTGGGCGT
CGAGCAGGACCCCGGCATCTCCGTAGTCCCGGGCCTCAATGGCACCGCGCGGATCGCCTCCTCGCCTC
TCGCCTCGTCGCCGCCTCTCTGGCTCTCGCGGGCGCCACCGCCGTCCCCGCCGTCGGGGCCCGAGACC
GCGGAGGCCGCGGCGCTGTTCAGCCGCGAATGCCGGCCGAGCCCCGCGCAGCTGGGCGCGCTGCGTGT
CATGCTGTGGGTCACCACCGCCTACTTCTTCCTGCCCTTTCTGTGCCTCAGCATCCTCTACGGGCTCA
TCGGGCGGGAGCTGTGGAGCAGCCGGCGGCCGCTGCGAGGCCCGGCCGCCTCGGGGCGGGAGAGAGGC
CACCGGCAGACCGTCCGCGTCCTGCgtaagtggagccgccgtggttccaaagacgcctgcctgcagtc
cgccccgccggggaccgcgcaaacgctccctccccttcccctgctcgcccagctctgggcgccgcttc
cagctcccttcctatttcgattccagcctccacccgccggtcattcccatcccccgagaaaaccatgt
cctgtcccccaggagctctgggggaccccagggcgctttgagggtgggatccccggatccgattcagt
aaccagcagtgcttttccagagcctctgagaccagaaaggagagttggtaattcttaatccaaccacc
tgttagatgccacaaatgaggagtcctcacagtgctcttgagaagacgagggagatttcattaagcta
aaattttttatttaatgttaagtgatgctgaaggctaaagtaaaccttgctcgtatcaaaaagtaaag
attgtgcagacctgttgtagaattcttttcaacagagaacagaaaacttgtctccgaagtgggtttgt
ggaaggaagcctgccaaggcggcttgttcagagaaattgctccttctggtttatgtccagccttgata
acacatatgggagcctactatgcagttttaaagcaagtatccatgcagcctgcagcctggtcattttt
tctggggtgaggatctgcctaggtagaagttttctctaatttattttgctgttacttgttattgcaga
tggttccttgtcggggtgggggtttatttgcttcccaatgcttttgttaatcccggtgctgtgtctt
atgttgcagTGGTGGTGGTTCTGGCATTTATAATTTGCTGGTTGCCCTTCCACGTTGGCAGAATCATT
TACATAAACACGGAAGATTCGCGGATGATGTACTTCTCTCAGTACTTTAACATCGTCGCTCTGCAACT
TTTCTATCTGAGCGCATCTATCAACCCAATCCTCTACAACCTCATTTCAAAGAAGTACAGAGCGGCGG
CCTTTAAACTGCTGCTCGCAAGGAAGTCCAGGCCGAGAGGCTTCCACAGAAGCAGGGACACTGCGGGG
GAAGTTGCAGGGGACACTGGAGGAGACACGGTGGGCTACACCGAGACAAGCGCTAACGTGAAGACGAT
GGGATAA

FIG. 1

ATGGGCAGCCCCTGGAACGGCAGCGACGGCCCCGAGGGGGCGCGGAGCCGCCGTGGCCCGCGCTG
CCGCCTTGCGACGAGCGCCGCTGCTCGCCCTTTCCCCTGGGGGCGCTGGTGCCGGTGACCGCTGTG
TGCCTGTGCCTGTTCGTCGTCGGGGTGAGCGGCAACGTGGTGACCGTGATGCTGATCGGGCGCTAC
CGGGACATGCGGACCACCACCAACTTGTACCTGGGCAGCATGGCCGTGTCCGACCTACTCATCCTG
CTCGGGCTGCCGTTCGACCTGTACCGCCTCTGGCGCTCGCGGCCCTGGGTGTTCGGGCCGCTGCTC
TGCCGCCTGTCCCTCTACGTGGGCGAGGGCTGCACCTACGCCACGCTGCTGCACATGACCGCGCTC
AGCGTCGAGCGCTACCTGGCCATCTGCCGCCCGCTCCGCGCCCGCGTCTTGGTCACCCGGCGCCGC
GTCCGCGCGCTCATCGCTGTGCTCTGGGCCGTGGCGCTGCTCTCTGCCGGTCCCTTCTTGTTCCTG
GTGGGCGTCGAGCAGGACCCCGGCATCTCCGTAGTCCCGGGCCTCAATGGCACCGCGCGGATCGCC
TCCTCGCCTCTCGCCTCGTCGCCGCCTCTCTGGCTCTCGCGGGCGCCACCGCCGTCCCCGCCGTCG
GGGCCCGAGACCGCGGAGGCCGCGGCGCTGTTCAGCCGCGAATGCCGGCCGAGCCCCGCGCAGCTG
GGCGCGCTGCGTGTCATGCTGTGGGTCACCACCGCCTACTTCTTCCTGCCCTTTCTGTGCCTCAGC
ATCCTCTACGGGCTCATCGGGCGGGAGCTGTGGAGCAGCCGGCGGCCGCTGCGAGGCCCGGCCGCC
TCGGGGCGGGAGAGAGGCCACCGGCAGACCGTCCGCGTCCTGCTGGTGGTGGTTCTGGCATTTATA
ATTTGCTGGTTGCCCTTCCACGTTGGCAGAATCATTTACATAAACACGGAAGATTCGCGGATGATG
TACTTCTCTCAGTACTTTAACATCGTCGCTCTGCAACTTTTCTATCTGAGCGCATCTATCAACCCA
ATCCTCTACAACCTCATTTCAAAGAAGTACAGAGCGGCGGCCTTTAAACTGCTGCTCGCAAGGAAG
TCCAGGCCGAGAGGCTTCCACAGAAGCAGGGACACTGCGGGGGAAGTTGCAGGGGACACTGGAGGA
GACACGGTGGGCTACACCGAGACAAGCGCTAACGTGAAGACGATGGGATAA

FIG.2

MGSPWNGSDGPEGAREPPWPALPPCDERRCSPFPLGALVPVTAVCLCLFVVGVSGNVVTVMLIGRY
RDMRTTTNLYLGSMAVSDLLILLGLPFDLYRLWRSRPWVFGPLLCRLSLYVGEGCTYATLLHMTAL
SVERYLAICRPLRARVLVTRRRVRALIAVLWAVALLSAGPFLFLVGVEQDPGISVVPGLNGTARIA
SSPLASSPPLWLSRAPPPSPPSGPETAEAAALFSRECRPSPAQLGALRVMLWVTTAYFFLPFLCLS
ILYGLIGRELWSSRRPLRGPAASGRERGHRQTVRVLLVVVLAFIICWLPFHVGRIIYINTEDSRMM
YFSQYFNIVALQLFYLSASINPILYNLISKXYRAAAFKLLLARKSRPRGFHRSRDTAGEVAGDTGG
DTVGYTETSANVKTMG

FIG.3

ATGGGCAGCCCCTGGAACGGCAGCGACGGCCCCGAGGGGGCGCGGGAGCCGCCGTGGCCCGCGCTG
CCGCCTTGCGACGAGCGCCGCTGCTCGCCCTTTCCCCTGGG&GCGCTGGTGCCGGTGACCGCTGTG
TGCCTGTGCCTGTTCGTCGTCGGGGTGAGCGGCAACGTGGTGACCGTGATGCTGATCGGGCGCTAC
CGGGACATGCGGACCACCACCAACTTGTACCTGGGCAGCATGGCCGTGTCCGACCTACTCATCCTG
CTCGGGCTGCCGTTCGACCTGTACCGCCTCTGGCGCTCGCGGCCCTGGGTGTTCGGGCCGCTGCTC
TGCCGCCTGTCCCTCTACGTGGGCGAGGGCTGCACCTACGCCACGCTGCTGCACATGACCGCGCTC
AGCGTCGAGCGCTACCTGGCCATCTGCCGCCCGCTCCGCGCCCGCGTCTTGGTCACCCGGCGCCGC
GTCCGCGCGCTCATCGCTGTGCTCTGGGCCGTGGCGCTGCTCTCTGCCGGTCCCTTCTTGTTCCTG
GTGGGCGTCGAGCAGGACCCCGGCATCTCCGTAGTCCCGGGCCTCAATGGCACCGCGCGGATCGCC
TCCTCGCCTCTCGCCTCGTCGCCGCCTCTCTGGCTCTCGCGGGCGCCACCGCCGTCCCCGCCGTCG
GGGCCCGAGACCGCGGAGGCCGCGGCGCTGTTCAGCCGCGAATGCCGGCCGAGCCCCGCGCAGCTG
GGCGCGCTGCGTGTCATGCTGTGGGTCACCACCGCCTACTTCTTCCTGCCCTTTCTGTGCCTCAGC
ATCCTCTACGGGCTCATCGGGCGGGAGCTGTGGAGCAGCCGGCGGCCGCTGCGAGGCCCGGCCGCC
TCGGGGCGGGAGAGAGGCCACCGGCAGACCGTCCGCGTCCTGCGTAAGTGGAGCCGCCGTGGTTCC
AAAGACGCCTGCCTGCAGTCCGCCCCGCCGGGGACCGCGCAAACGCTGGGTCCCCTTCCCCTGCTC
GCCCAGCTCTGGGCGCCGCTTCCAGCTCCCTTTCCTATTTCGATTCCAGCCTCCACCCGCCGTGGT
GGTGGTTCTGGCATTTATAATTTGCTGGTTGCCCTTCCACGTTGGCAGAATCATTTACATAAACAC
GGAAGATTCGCGGATGATGTACTTCTCTCAGTACTTTAACATCGTCGCTCTGCAACTTTTCTATCT
GAGCGCATCTATCAACCCAATCCTCTACAACCTCATTTCAAAGAAGTACAGAGCGGCGGCCTTTAA
ACTGCTGCTCGCAAGGAAGTCCAGGCCGAGAGGCTTCCACAGAAGCAGGGACACTGCGGGGGAAGT
TGCAGGGGACACTGGAGGAGACACGGTGGGCTACACCGAGACAAGCGCTAACGTGAAGACGATGGG
ATAA

FIG.4

MGSPWNGSDGPEGAREPPWPALPPCDERRCSPFPLGALVPVTAVCLCLFVVGVSGNVVIVMLIGRY
RDMRTTTNLYLGSMAVSDLLILLGLPFDLYRLWRSRPWVFGPLLCRLSLYVGEGCTYATLLHMTAL
SVERYLAICRPLRARVLVTRRRVRALIAVLWAVALLSAGPFLFLVGVEQDPGISVVPGLNGTARIA
SSPLASSPPLWLSRAPPPSPPSGPETAEAAALFSRECRPSPAQLGALRVMLWVTTAYFFLPFLCLS
ILYGLIGRELWSSRRPLRGPAASGRERGHRQTVRVLRKWSRRGSKDACLQSAPPGTAQTLGPLPLL
AQLWAPLPAPFPISIPASTRRGGGSGIYNLLVALPRWQNHLHKHGRFADDVLLSVL

FIG.5

```
  ATG GGC AGC CCC TGG AAC GGC AGC GAC GGC CCC GAG GGG GCG CGG GAG CCG CCG TGG CCC GCG CTG CCG CCT TGC
1 M   G   S   P   W   N   G   S   D   G   P   E   G   A   R   E   P   P   W   P   A   L   P   P   C
                                                TM1
  GAC GAG CGC CGC TGC TCG CCC TTT CCC CTG GGG GCG CTG GTG CCG GTG ACC GCT GTG TGC CTG TGC CTG TTC GTC
  D   E   R   R   C   S   P   F   P   L   G   A   L   V   P   V   T   A   V   C   L   C   L   F   V

  GTC GGG GTG AGC GGC AAC GTG GTG ACC GTG ATG CTG ATC GGG CGC TAC CGG GAC ATG CGG ACC ACC ACC AAC TTG
  V   G   V   S   G   N   V   V   T   V   M   L   I   G   R   Y   R   D   M   R   T   T   T   N   L
              TM2
  TAC CTG GGC AGC ATG GCC GTG TCC GAC CTA CTC ATC CTG CTC GGG CTG GAC TTC GAC CTG TAC CGC CTC TGG CGC
  Y   L   G   S   M   A   V   S   D   L   L   I   L   L   G   L   P   F   D   L   Y   R   L   W   R
                                            TM3
  TCG CGG CCC TGG GTG TTC GGG CCG CTG CTC TGC CGC CTG TCC CTC TAC GTG GGC GAG GGC TGC ACC TAC GCC ACG
  S   R   P   W   V   F   G   P   L   L   C   R   L   S   L   Y   V   G   E   G   C   T   Y   A   T

  CTG CTG CAC ATG ACC GCG CTC AGC GTC GAG CGC TAC CTG GCC ATC TGC CGC CCG CTC CGC GCC CGC GTC TTG GTC
  L   L   H   M   T   A   L   S   V   E   R   Y   L   A   I   C   R   P   L   R   A   R   V   L   V
                                TM4
  ACC CGG CGC CGC GTC CGC GCG CTC ATC GCT GTG CTC TGG GCC GTG GCG CTG CTC TCT GCC GGT CCC TTC TTG TTC
  T   R   R   R   V   R   A   L   I   A   V   L   W   A   V   A   L   L   S   A   G   P   F   L   F

  CTG GTG GGC GTC GAG CAG GAC CCC GGC ATC TCC GTA GTC CCG GGC CTC AAT GGC ACC GCG CGG ATC GCC TCC TCG
  L   V   G   V   E   Q   D   P   G   I   S   V   V   P   G   L   N   G   T   A   R   I   A   S   S

  CCT CTC GCC TCG TCG CCG CCT CTC TGG CTC TCG CGG GCG CCA CCG CCG TCC CCG CCG TCG GGG CCC GAG ACC GCG
  P   L   A   S   S   P   P   L   W   L   S   R   A   P   P   P   S   P   P   S   G   P   E   T   A
                                                                                    TM5
  GAG GCC GCG GCG CTG TTC AGC CGC GAA TGC CGG CCG AGC CCC GCG CAG CTG GGC GCG CTG CGT GTC ATG CTG TGG
  E   A   A   A   L   F   S   R   E   C   R   P   S   P   A   Q   L   G   A   L   R   V   M   L   W

  GTC ACC ACC GCC TAC TTC TTC CTG CCC TTT CTG TGC CTC AGC ATC CTC TAC GGG CTC ATC GGG CGG GAG CTG TGG
  V   T   T   A   Y   F   F   L   P   F   L   C   L   S   I   L   Y   G   L   I   G   R   E   L   W

  AGC AGC CGG CGG CCG CTG CGA GGC CCG GCC GCC TCG GGG CGG GAG AGA GGC CAC CGG CAG ACC GTC CGC GTC CTG
  S   S   R   R   P   L   R   G   P   A   A   S   G   R   E   R   G   H   R   Q   T   V   R   V   L
```

FIG.6A

```
(Donor A)
CgtAAGTGGAGCCGCCGTGGTTCCAAAGACGCCTGCCTGCAGTCCGCCCCGCCGGGGACCGCGCAAACGCTGGGTCCCCT
TCCCCTGCTCGCCCAGCTCTGGGCGCCGCTTCCAGCTCCCTTTCCTATTTCGATTCCAGCCTCCACCCGCCGgt...+569 bp
                                                                          (Donor B)
FM-1A:  7TM, 403  amino acids
                   TM6
                 ag/CTG GTG GTG GTT CTG GCA TTT ATA ATT TGC TGG TTG CCC TTC CAC GTT GGC AGA ATC
                     L   V   V   V   L   A   F   I   I   C   W   L   P   F   H   V   O   R   I
                                                 TM7
        ATT TAC ATA AAC ACG GAA GAT TCG CGG ATG ATG TAC TTC TCT CAG TAC TTT AAC ATC GTC GCT CTG CAA CTT TTC
         I   Y   I   N   T   E   D   S   R   M   M   Y   F   S   Q   Y   F   N   I   V   A   L   Q   L   F

        TAT CTG AGC GCA TCT ATC AAC CCA ATC CTC TAC AAC CTC ATT TCA AAG AAG TAC AGA GCG GCG GCC TTT AAA CTG
         Y   L   S   A   S   I   N   P   I   L   Y   N   L   I   S   K   K   Y   R   A   A   A   F   K   L

        CTG CTC GCA AGG AAG TCC AGG CCG AGA GGC TTC CAC AGA AGC AGG GAC ACT GCG GGG GAA GTT GCA GGG GAC ACT
         L   L   A   R   K   S   R   P   R   G   F   H   R   S   R   D   T   A   G   E   V   A   G   D   T

        GGA GGA GAC ACG GTG GGC TAC ACC GAG ACA AGC GCT AAC GTG AAG ACG ATG GGA TAA
         G   G   D   T   V   G   Y   T   E   T   S   A   N   V   K   T   M   G   *                  403
```

FIG.6B

FM-1B: 5TM, 387 amino acids

```
  CGT AAG TGG AGC CGC CGT GGT TCC AAA GAC GCC TGC CTG CAG TCC GCC CCG CCG GGG ACC GCG CAA ACG CTG
  R   K   W   S   R   R   G   S   K   D   A   C   L   Q   S   A   P   P   G   T   A   Q   T   L

GGT CCC CTT CCC CTG CTC GCC CAG CTC TGG GCG CCG CTT CCA GCT CCC TTT CCT ATT TCG ATT CCA GCC TCC ACC
G   P   L   P   L   L   A   Q   L   W   A   P   L   P   A   P   F   P   I   S   I   P   A   S   T

CGC CGT GGT GGT GGT TCT GGC ATT TAT AAT TTG CTG GTT GCC CTT CCA CGT TGG CAG AAT CAT TTA CAT AAA CAC
R   R   G   G   G   S   G   I   Y   N   L   L   V   A   L   P   R   W   Q   N   H   L   H   K   H

GGA AGA TTC GCG GAT GAT GTA CTT CTC TCA GTA CTT TAA
G   R   F   A   D   D   V   L   L   S   V   L   *                                          387
```

FIG.6C

ATGCCCTGGACCAGACCCCAGGTGGACCTCCATGCTGCTGCAGCAGAGACCATGGACCAGTACACC
ACGGACGACCACCACTACGAGGGCTCCCTCTTCCCCGCGTCCACCCTCATCCCCGTCACGGTCATC
TGCATCCTCATCTTCGTGGTCGGCGTGACCGGCAACACCATGACCATCCTCATCATCCAGTACTTC
AAGGACATGAAGACCACCACCAACCTGTACCTGTCCAGCATGGCCGTGTCCGACCTCGTCATCTTC
CTCTGCCTGCCCTTCGACCTGTACCGCCTGTGGAAGTACGTGCCGTGGCTGTTCGGCGAGGCCGTG
TGCCGCCTCTACCACTACATCTTCGAAGGCTGCACGTCGGCCACCATCCTCCACATCACGGCCCTG
AGCATCGAGCGCTACCTGGCCATCAGCTTCCCCCTCAGGAGCAAGGTGATGGTGACCAGGAGAAGG
GTCCAGTACATCATCCTGGCCCTGTGGTGCTTCGCCCTGGTGTCGGCCGCTCCCACGCTCTTCCTG
GTCGGGGTGGAGTACGACAACGAGACGCACCCCGACTACAACACGGGCCAGTGCAAGCACACGGGC
TACGCCATCAGCTCGGGGCAGCTGCACATCATGATCTGGGTGTCCACCACCTACTTCTTCTGCCCG
ATGCTGTGTCTCCTCTTCCTCTACGGCTCCATCGGGTGCAAGCTGTGGAAGAGCAAGAACGACCTG
CAGGGCCCGTGCGCCCTGGCCCGCGAGAGGTCGCACAGGCAAACGGTGAAGATCCTGGTGGTGGTG
GTGCTGGCCTTCATCATCTGCTGGCTGCCCTACCACATCGGCAGGAACCTGTTCGCCCAGGTGGAC
GACTACGACACGGCCATGCTCAGCCAGAATTTCAACATGGCCTCCATGGTGCTCTGCTACCTCAGC
GCCTCCATCAACCCCGTCGTCTACAACCTGATGTCGAGGAAGTACCGGGCCGCCGCCAAGCGCCTC
TTCCTGCTCCACCAGAGACCCAAGCCGGCCCACCGGGGGCAGGGGCAGTTTTGCATGATCGGCCAC
AGCCCCACCCTGGACGAGAGCCTGACGGGGGTGTGA

FIG.7

MPWTRPQVDLHAAAAETMDQYTTDDHHYEGSLFPASTLIPVTVICILIF W GVTGNT
MTILIIQYFKDMKTTTNLYLSSMAVSDLVIFLCLPFDLYRLWKYVPWLFGEAVCRLY
HYIFEGCTSATILHITALSIERYLAISFPLRSKVMVTRRRVQYIILALWCFALVSAA
PTLFLVGVEYDNETHPDYNTGQCKHTGYAISSGQLHIMIWVSTTYFFCPMLCLLFLY
GSIGCKLWKSKNDLQGPCALARERSHRQTVKILVVVVLAFIICWLPYHIGRNLFAQV
DDYDTAMLSQNFNMASMVLCYLSASINPVVYNLMSRKYRAAAKRLFLLHQRPKPAHR
GQGQFCMIGHSPTLDESLTGV

FIG.8

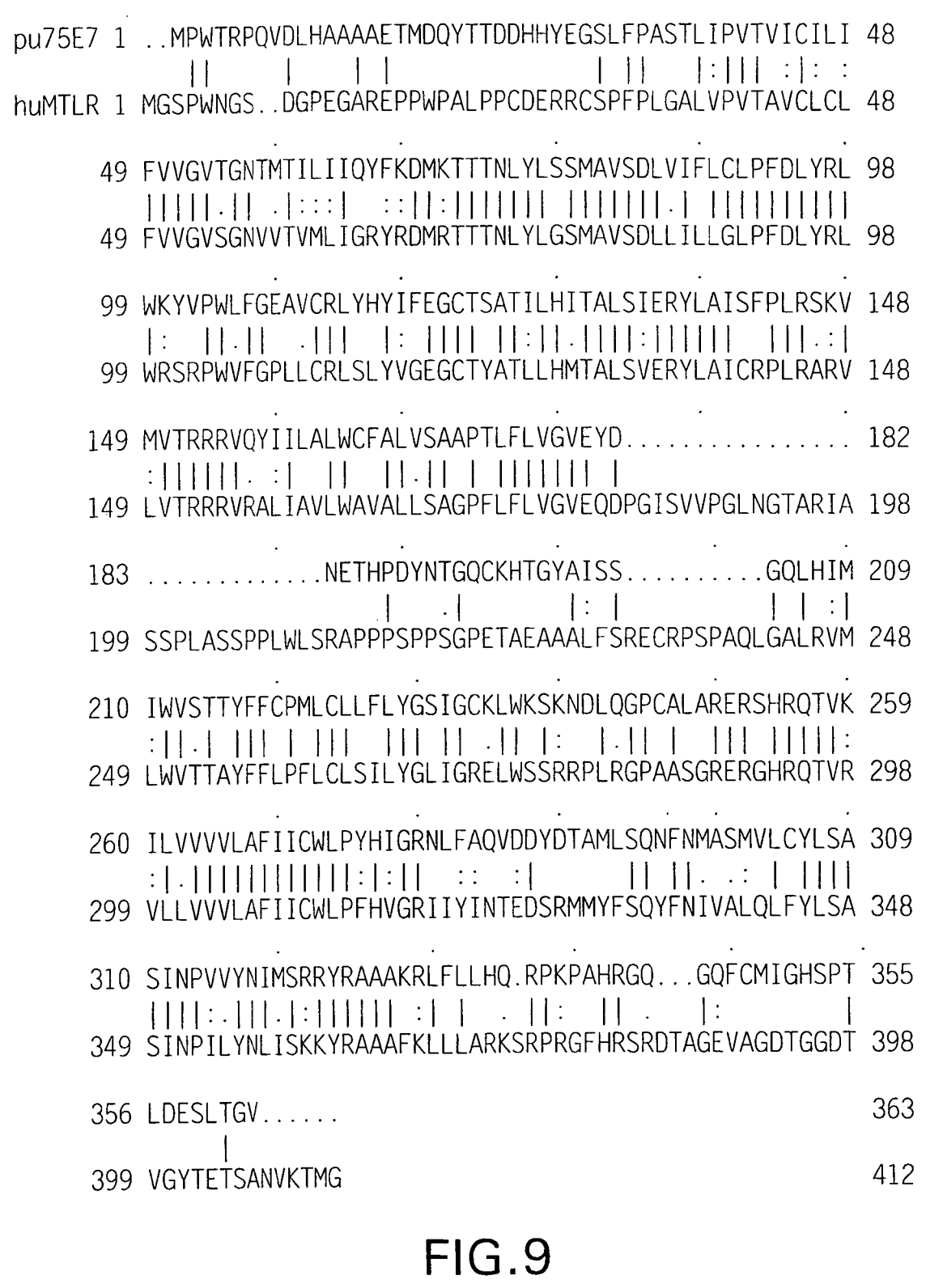

```
pu75E7 1 ..MPWTRPQVDLHAAAAETMDQYTTDDHHYEGSLFPASTLIPVTVICILI 48
huMTLR 1 MGSPWNGS..DGPEGAREPPWPALPPCDERRCSPFPLGALVPVTAVCLCL 48

49 FVVGVTGNTMTILIIQYFKDMKTTTNLYLSSMAVSDLVIFLCLPFDLYRL 98
49 FVVGVSGNVVTVMLIGRYRDMRTTTNLYLGSMAVSDLLILLGLPFDLYRL 98

99 WKYVPWLFGEAVCRLYHYIFEGCTSATILHITALSIERYLAISFPLRSKV 148
99 WRSRPWVFGPLLCRLSLYVGEGCTYATLLHMTALSVERYLAICRPLRARV 148

149 MVTRRRVQYIILALWCFALVSAAPTLFLVGVEYD................ 182
149 LVTRRRVRALIAVLWAVALLSAGPFLFLVGVEQDPGISVVPGLNGTARIA 198

183 .............NETHPDYNTGQCKHTGYAISS..........GQLHIM 209
199 SSPLASSPPLWLSRAPPPSPPSGPETAEAAALFSRECRPSPAQLGALRVM 248

210 IWVSTTYFFCPMLCLLFLYGSIGCKLWKSKNDLQGPCALARERSHRQTVK 259
249 LWVTTAYFFLPFLCLSILYGLIGRELWSSRRPLRGPAASGRERGHRQTVR 298

260 ILVVVVLAFIICWLPYHIGRNLFAQVDDYDTAMLSQNFNMASMVLCYLSA 309
299 VLLVVVLAFIICWLPFHVGRIIYINTEDSRMMYFSQYFNIVALQLFYLSA 348

310 SINPVVYNIMSRRYRAAAKRLFLLHQ.RPKPAHRGQ...GQFCMIGHSPT 355
349 SINPILYNLISKKYRAAAFKLLLARKSRPRGFHRSRDTAGEVAGDTGGDT 398

356 LDESLTGV...... 363
399 VGYTETSANVKTMG 412
```

FIG.9

SEQUENCE LISTING

```
<160> NUMBER OF SEQ ID NOS: 15

<210> SEQ ID NO 1
<211> LENGTH: 3066
<212> TYPE: DNA
<213> ORGANISM: Homo sapiens
```

-continued

<400> SEQUENCE: 1
ttgaaattat ctggtcactg ccgggcgcgg tggctcacgc ctgtaatccc agcactttgg 60
gaggtcgagg cgggtggacc acctggggtc aggagttcga gaccaggctg gccaacatgg 120
cgaaaccctg actacacaaa aaacacaaaa tttagccggg gcttgggcgc tcctgtgctc 180
ccagctactc aggaggctga ggtgggagga ctgcttgagc ctgggaggtc gaggctgcag 240
tgagctgtga tcgcgccact taaactccag cctggacgac agtgagaccc tgtctcaaga 300
agaaaaaaag aaagaaagaa agaaaaaaag aaaaaaaaga aattatttgg tcaattatat 360
ggtcagctcc ctccaccact cgcgaattta cagaagagga gaactgggct gggcgagacc 420
aggactagcc caagattaca caagttactc ggttgtagag ccaggattag acaggagagg 480
ctctagattc tggtctagac tcccctccta ttatttagca ttatggcttc ctgaggatta 540
ccatgagccc tcctccaccg tcaagcggca gctaccagcc accagaccag atcccttcga 600
aggtgcccgg agtaccagac tgacaaaagc gcccgtacag tgctcagtcc tgtaaccaaa 660
gctgtctagg gtgcagacat cgctcaccgg accgggtagg gctcgtgcgc taagggcgcc 720
gggtattcca gttagtggag agggaagcgc cctggaactg catgggcccg ggagagggcg 780
cgggagcgga gcatggccgg gccggggcgg gccgcggccg tgggcggaga ctgcgcgcag 840
ctagctcggg agcgcctcgg agcccacccc gcagagccgc ttctcgcgcc ccgcagcgca 900
gcgcagcgct ccgccgtctg acctgccgcg cccgcagcgt gcgggctggg aaaggaggcg 960
ctcaccgaga gggaccacgc gccaggctcc cagcccgacc cgggacgcgg cggccgcgcg 1020
gagcacccat gggcagcccc tggaacggca gcgacggccc cgaggggggcg cgggagccgc 1080 cgtggcccgc gctgccgcct tgcgacgagc gccgctgctc gccctttccc ctgggggcgc 1140
tggtgccggt gaccgctgtg tgcctgtgcc tgttcgtcgt cggggtgagc ggcaacgtgg 1200
tgaccgtgat gctgatcggg cgctaccggg acatgcggac caccaccaac ttgtacctgg 1260
gcagcatggc cgtgtccgac ctactcatcc tgctcgggct gccgttcgac ctgtaccgcc 1320
tctggcgctc gcggccctgg gtgttcgggc cgctgctctg ccgcctgtcc ctctacgtgg 1380
gcgagggctg cacctacgcc acgctgctgc acatgaccgc gctcagcgtc gagcgctacc 1440
tggccatctg ccgcccgctc cgcgcccgcg tcttggtcac ccggcgccgc gtccgcgcgc 1500
tcatcgctgt gctctgggcc gtggcgctgc tctctgccgg tcccttcttg ttcctggtgg 1560
gcgtcgagca ggaccccggc atctccgtag tcccgggcct caatggcacc gcgcggatcg 1620
cctcctcgcc tctcgcctcg tcgccgcctc tctggctctc gcgggcgcca ccgccgtccc 1680
cgccgtcggg gcccgagacc gcggaggccg cggcgctgtt cagccgcgaa tgccggccga 1740
gccccgcgca gctgggcgcg ctgcgtgtca tgctgtgggt caccaccgcc tacttcttcc 1800
tgccctttct gtgcctcagc atcctctacg ggctcatcgg gcgggagctg tggagcagcc 1860
ggcggccgct gcgaggcccg gccgcctcgg ggcgggagag aggccaccgg cagaccgtcc 1920
gcgtcctgcg taagtggagc cgccgtggtt ccaaagacgc ctgcctgcag tccgccccgc 1980
cggggaccgc gcaaacgctg ggtccccttc ccctgctcgc ccagctctgg gcgccgcttc 2040
cagctccctc ctatttcgat tccagcctcc acccgccggt acttcccatc ccccgagaaa 2100
accatgtcct gtcccccagg agctctgggg gaccccaggg cgctttgagg gtgggatccc 2160
cggatccgat tcagtaacca gcagtgcttt tccagagcct ctgagaccag aaaggagagt 2220
tggtaattct taatccaacc acctgttaga tgccacaaat gaggagtcct cacagtgctc 2280
ttgagaagac gagggagatt tcattaagct aaaatttttt atttaatgtt aagtgatgct 2340

-continued

```
gaaggctaaa gtaaaccttg ctcgtatcaa aaagtaaaga ttgtgcagac ctgttgtaga   2400

attcttttca acagagaaca gaaaacttgt ctccgaagtg ggtttgtgga aggaagcctg   2460

ccaaggcggc ttgttcagag aaattgctcc ttctggttta tgtccagcct tgataacaca   2520

tatgggagcc tactatgcag ttttaaagca agtatccatg cagcctgcag cctggtcatt   2580

ttttctgggg tgaggatctg cctaggtaga agttttctct aatttatttt gctgttactt   2640

gttattgcag atggttcctt gtcggggtgg ggggtttatt tgcttcccaa tgcttttgtt   2700

aatcccggtg ctgtgtctta tgttgcagtg gtggtggttc tggcatttat aatttgctgg   2760

ttgcccttcc acgttggcag aatcatttac ataaacacgg aagattcgcg gatgatgtac   2820

ttctctcagt actttaacat cgtcgctctg caacttttct atctgagcgc atctatcaac   2880

ccaatcctct acaacctcat ttcaaagaag tacagagcgg cggcctttaa actgctgctc   2940

gcaaggaagt ccaggccgag aggcttccac agaagcaggg acactgcggg ggaagttgca   3000

ggggacactg gaggagacac ggtgggctac accgagacaa gcgctaacgt gaagacgatg   3060

ggataa                                                              3066
```

<210> SEQ ID NO 2
<211> LENGTH: 1239
<212> TYPE: DNA
<213> ORGANISM: Homo sapiens

<400> SEQUENCE: 2

```
atgggcagcc cctggaacgg cagcgacggc cccgaggggg cgcgggagcc gccgtggccc     60

gcgctgccgc cttgcgacga gcgccgctgc tcgccctttc ccctgggggc gctggtgccg    120

gtgaccgctg tgtgcctgtg cctgttcgtc gtcggggtga gcggcaacgt ggtgaccgtg    180

atgctgatcg ggcgctaccg ggacatgcgg accaccacca acttgtacct gggcagcatg    240

gccgtgtccg acctactcat cctgctcggg ctgccgttcg acctgtaccg cctctggcgc    300

tcgcggccct gggtgttcgg gccgctgctc tgccgcctgt ccctctacgt gggcgagggc    360

tgcacctacg ccacgctgct gcacatgacc gcgctcagcg tcgagcgcta cctggccatc    420

tgccgcccgc tccgcgcccg cgtcttggtc acccggcgcc gcgtccgcgc gctcatcgct    480

gtgctctggg ccgtggcgct gctctctgcc ggtcccttct tgttcctggt gggcgtcgag    540

caggaccccg gcatctccgt agtcccgggc ctcaatggca ccgcgcggat cgcctcctcg    600

cctctcgcct cgtcgccgcc tctctggctc tcgcgggcgc caccgccgtc cccgccgtcg    660

gggcccgaga ccgcggaggc cgcggcgctg ttcagccgcg aatgccggcc gagccccgcg    720

cagctgggcg cgctgcgtgt catgctgtgg gtcaccaccg cctacttctt cctgcccttt    780

ctgtgcctca gcatcctcta cgggctcatc gggcgggagc tgtggagcag ccggcggccg    840

ctgcgaggcc cggccgcctc ggggcgggag agaggccacc ggcagaccgt ccgcgtcctg    900

ctggtggtgg ttctggcatt tataatttgc tggttgccct tccacgttgg cagaatcatt    960

tacataaaca cggaagattc gcggatgatg tacttctctc agtactttaa catcgtcgct   1020

ctgcaacttt tctatctgag cgcatctatc aacccaatcc tctacaacct catttcaaag   1080

aagtacagag cggcggcctt taaactgctg ctcgcaagga agtccaggcc gagaggcttc   1140

cacagaagca gggacactgc gggggaagtt gcaggggaca ctggaggaga cacggtgggc   1200

tacaccgaga caagcgctaa cgtgaagacg atgggataa                           1239
```

-continued

```
<210> SEQ ID NO 3
<211> LENGTH: 412
<212> TYPE: PRT
<213> ORGANISM: Homo sapiens

<400> SEQUENCE: 3

Met Gly Ser Pro Trp Asn Gly Ser Asp Gly Pro Glu Gly Ala Arg Glu
 1               5                  10                  15

Pro Pro Trp Pro Ala Leu Pro Pro Cys Asp Glu Arg Arg Cys Ser Pro
            20                  25                  30

Phe Pro Leu Gly Ala Leu Val Pro Val Thr Ala Val Cys Leu Cys Leu
        35                  40                  45

Phe Val Val Gly Val Ser Gly Asn Val Val Thr Val Met Leu Ile Gly
    50                  55                  60

Arg Tyr Arg Asp Met Arg Thr Thr Thr Asn Leu Tyr Leu Gly Ser Met
65                  70                  75                  80

Ala Val Ser Asp Leu Leu Ile Leu Leu Gly Leu Pro Phe Asp Leu Tyr
                85                  90                  95

Arg Leu Trp Arg Ser Arg Pro Trp Val Phe Gly Pro Leu Leu Cys Arg
            100                 105                 110

Leu Ser Leu Tyr Val Gly Glu Gly Cys Thr Tyr Ala Thr Leu Leu His
        115                 120                 125

Met Thr Ala Leu Ser Val Glu Arg Tyr Leu Ala Ile Cys Arg Pro Leu
    130                 135                 140

Arg Ala Arg Val Leu Val Thr Arg Arg Arg Val Arg Ala Leu Ile Ala
145                 150                 155                 160

Val Leu Trp Ala Val Ala Leu Leu Ser Ala Gly Pro Phe Leu Phe Leu
                165                 170                 175

Val Gly Val Glu Gln Asp Pro Gly Ile Ser Val Val Pro Gly Leu Asn
            180                 185                 190

Gly Thr Ala Arg Ile Ala Ser Ser Pro Leu Ala Ser Ser Pro Pro Leu
        195                 200                 205

Trp Leu Ser Arg Ala Pro Pro Pro Ser Pro Pro Ser Gly Pro Glu Thr
    210                 215                 220

Ala Glu Ala Ala Ala Leu Phe Ser Arg Glu Cys Arg Pro Ser Pro Ala
225                 230                 235                 240

Gln Leu Gly Ala Leu Arg Val Met Leu Trp Val Thr Thr Ala Tyr Phe
                245                 250                 255

Phe Leu Pro Phe Leu Cys Leu Ser Ile Leu Tyr Gly Leu Ile Gly Arg
            260                 265                 270

Glu Leu Trp Ser Ser Arg Arg Pro Leu Arg Gly Pro Ala Ala Ser Gly
        275                 280                 285

Arg Glu Arg Gly His Arg Gln Thr Val Arg Val Leu Leu Val Val Val
    290                 295                 300

Leu Ala Phe Ile Ile Cys Trp Leu Pro Phe His Val Gly Arg Ile Ile
305                 310                 315                 320

Tyr Ile Asn Thr Glu Asp Ser Arg Met Met Tyr Phe Ser Gln Tyr Phe
                325                 330                 335

Asn Ile Val Ala Leu Gln Leu Phe Tyr Leu Ser Ala Ser Ile Asn Pro
            340                 345                 350

Ile Leu Tyr Asn Leu Ile Ser Lys Lys Tyr Arg Ala Ala Ala Phe Lys
        355                 360                 365

Leu Leu Leu Ala Arg Lys Ser Arg Pro Arg Gly Phe His Arg Ser Arg
    370                 375                 380
```

```
Asp Thr Ala Gly Glu Val Ala Gly Asp Thr Gly Gly Asp Thr Val Gly
385                 390                 395                 400

Tyr Thr Glu Thr Ser Ala Asn Val Lys Thr Met Gly
                405                 410


<210> SEQ ID NO 4
<211> LENGTH: 1390
<212> TYPE: DNA
<213> ORGANISM: Homo sapiens

<400> SEQUENCE: 4

atgggcagcc cctggaacgg cagcgacggc cccgaggggg cgcgggagcc gccgtggccc      60

gcgctgccgc cttgcgacga gcgccgctgc tcgccctttc cctgggggc gctggtgccg      120

gtgaccgctg tgtgcctgtg cctgttcgtc gtcggggtga gcggcaacgt ggtgaccgtg     180

atgctgatcg ggcgctaccg ggacatgcgg accaccacca acttgtacct gggcagcatg     240

gccgtgtccg acctactcat cctgctcggg ctgccgttcg acctgtaccg cctctggcgc     300

tcgcggccct gggtgttcgg gccgctgctc tgccgcctgt ccctctacgt gggcgagggc     360

tgcacctacg ccacgctgct gcacatgacc gcgctcagcg tcgagcgcta cctggccatc     420

tgccgcccgc tccgcgcccg cgtcttggtc acccggcgcc gcgtccgcgc gctcatcgct     480

gtgctctggg ccgtggcgct gctctctgcc ggtcccttct tgttcctggt gggcgtcgag     540

caggaccccg gcatctccgt agtcccgggc ctcaatggca ccgcgcggat cgcctcctcg     600

cctctcgcct cgtcgccgcc tctctggctc tcgcgggcgc caccgccgtc cccgccgtcg     660

gggcccgaga ccgcggaggc cgcggcgctg ttcagccgcg aatgccggcc gagccccgcg     720

cagctgggcg cgctgcgtgt catgctgtgg gtcaccaccg cctacttctt cctgcccttt     780

ctgtgcctca gcatcctcta cggctcatc gggcgggagc tgtggagcag ccggcggccg      840

ctgcgaggcc cggccgcctc ggggcgggag agaggccacc ggcagaccgt ccgcgtcctg     900

cgtaagtgga gccgccgtgg ttccaaagac gcctgcctgc agtccgcccc gccggggacc     960

gcgcaaacgc tgggtcccct tcccctgctc gcccagctct gggcgccgct tccagctccc    1020

tttcctattt cgattccagc ctccacccgc cgtggtggtg gttctggcat ttataatttg    1080

ctggttgccc ttccacgttg gcagaatcat ttacataaac acggaagatt cgcggatgat    1140

gtacttctct cagtacttta acatcgtcgc tctgcaactt ttctatctga gcgcatctat    1200

caacccaatc ctctacaacc tcatttcaaa gaagtacaga gcggcggcct ttaaactgct    1260

gctcgcaagg aagtccaggc cgagaggctt ccacagaagc agggacactg cgggggaagt    1320

tgcaggggac actggaggag acacggtggg ctacaccgag acaagcgcta acgtgaagac    1380

gatgggataa                                                           1390


<210> SEQ ID NO 5
<211> LENGTH: 386
<212> TYPE: PRT
<213> ORGANISM: Homo sapiens

<400> SEQUENCE: 5

Met Gly Ser Pro Trp Asn Gly Ser Asp Gly Pro Glu Gly Ala Arg Glu
 1               5                  10                  15

Pro Pro Trp Pro Ala Leu Pro Pro Cys Asp Glu Arg Arg Cys Ser Pro
            20                  25                  30

Phe Pro Leu Gly Ala Leu Val Pro Val Thr Ala Val Cys Leu Cys Leu
        35                  40                  45
```

-continued

```
Phe Val Val Gly Val Ser Gly Asn Val Val Thr Val Met Leu Ile Gly
    50                  55                  60

Arg Tyr Arg Asp Met Arg Thr Thr Thr Asn Leu Tyr Leu Gly Ser Met
65                  70                  75                  80

Ala Val Ser Asp Leu Leu Ile Leu Leu Gly Leu Pro Phe Asp Leu Tyr
                85                  90                  95

Arg Leu Trp Arg Ser Arg Pro Trp Val Phe Gly Pro Leu Leu Cys Arg
            100                 105                 110

Leu Ser Leu Tyr Val Gly Glu Gly Cys Thr Tyr Ala Thr Leu Leu His
        115                 120                 125

Met Thr Ala Leu Ser Val Glu Arg Tyr Leu Ala Ile Cys Arg Pro Leu
    130                 135                 140

Arg Ala Arg Val Leu Val Thr Arg Arg Arg Val Arg Ala Leu Ile Ala
145                 150                 155                 160

Val Leu Trp Ala Val Ala Leu Leu Ser Ala Gly Pro Phe Leu Phe Leu
                165                 170                 175

Val Gly Val Glu Gln Asp Pro Gly Ile Ser Val Val Pro Gly Leu Asn
            180                 185                 190

Gly Thr Ala Arg Ile Ala Ser Ser Pro Leu Ala Ser Ser Pro Pro Leu
        195                 200                 205

Trp Leu Ser Arg Ala Pro Pro Pro Ser Pro Pro Ser Gly Pro Glu Thr
    210                 215                 220

Ala Glu Ala Ala Ala Leu Phe Ser Arg Glu Cys Arg Pro Ser Pro Ala
225                 230                 235                 240

Gln Leu Gly Ala Leu Arg Val Met Leu Trp Val Thr Thr Ala Tyr Phe
                245                 250                 255

Phe Leu Pro Phe Leu Cys Leu Ser Ile Leu Tyr Gly Leu Ile Gly Arg
            260                 265                 270

Glu Leu Trp Ser Ser Arg Arg Pro Leu Arg Gly Pro Ala Ala Ser Gly
        275                 280                 285

Arg Glu Arg Gly His Arg Gln Thr Val Arg Val Leu Arg Lys Trp Ser
    290                 295                 300

Arg Arg Gly Ser Lys Asp Ala Cys Leu Gln Ser Ala Pro Pro Gly Thr
305                 310                 315                 320

Ala Gln Thr Leu Gly Pro Leu Pro Leu Leu Ala Gln Leu Trp Ala Pro
                325                 330                 335

Leu Pro Ala Pro Phe Pro Ile Ser Ile Pro Ala Ser Thr Arg Arg Gly
            340                 345                 350

Gly Gly Ser Gly Ile Tyr Asn Leu Leu Val Ala Leu Pro Arg Trp Gln
        355                 360                 365

Asn His Leu His Lys His Gly Arg Phe Ala Asp Asp Val Leu Leu Ser
    370                 375                 380

Val Leu
385
```

<210> SEQ ID NO 6
<211> LENGTH: 1092
<212> TYPE: DNA
<213> ORGANISM: Spheroides nephelus

<400> SEQUENCE: 6

```
atgccctgga ccagacccca ggtggacctc catgctgctg cagcagagac catggaccag     60

tacaccacgg acgaccacca ctacgagggc tccctcttcc ccgcgtccac cctcatcccc    120

gtcacggtca tctgcatcct catcttcgtg gtcggcgtga ccggcaacac catgaccatc    180
```

-continued

```
ctcatcatcc agtacttcaa ggacatgaag accaccacca acctgtacct gtccagcatg     240

gccgtgtccg acctcgtcat cttcctctgc ctgcccttcg acctgtaccg cctgtggaag     300

tacgtgccgt ggctgttcgg cgaggccgtg tgccgcctct accactacat cttcgaaggc     360

tgcacgtcgg ccaccatcct ccacatcacg gccctgagca tcgagcgcta cctggccatc     420

agcttccccc tcaggagcaa ggtgatggtg accaggagaa gggtccagta catcatcctg     480

gccctgtggt gcttcgccct ggtgtcggcc gctcccacgc tcttcctggt cggggtggag     540

tacgacaacg agacgcaccc cgactacaac acgggccagt gcaagcacac gggctacgcc     600

atcagctcgg ggcagctgca catcatgatc tgggtgtcca ccacctactt cttctgcccg     660

atgctgtgtc tcctcttcct ctacggctcc atcgggtgca agctgtggaa gagcaagaac     720

gacctgcagg gcccgtgcgc cctggcccgc gagaggtcgc acaggcaaac ggtgaagatc     780

ctggtggtgg tggtgctggc cttcatcatc tgctggctgc cctaccacat cggcaggaac     840

ctgttcgccc aggtggacga ctacgacacg gccatgctca gccagaattt caacatggcc     900

tccatggtgc tctgctacct cagcgcctcc atcaaccccg tcgtctacaa cctgatgtcg     960

aggaagtacc gggccgccgc caagcgcctc ttcctgctcc accagagacc caagccggcc    1020

caccgggggc aggggcagtt ttgcatgatc ggccacagcc ccaccctgga cgagagcctg    1080

acgggggtgt ga                                                        1092


<210> SEQ ID NO 7
<211> LENGTH: 363
<212> TYPE: PRT
<213> ORGANISM: Spheroides nephelus

<400> SEQUENCE: 7

Met Pro Trp Thr Arg Pro Gln Val Asp Leu His Ala Ala Ala Ala Glu
 1               5                  10                  15

Thr Met Asp Gln Tyr Thr Thr Asp Asp His His Tyr Glu Gly Ser Leu
            20                  25                  30

Phe Pro Ala Ser Thr Leu Ile Pro Val Thr Val Ile Cys Ile Leu Ile
        35                  40                  45

Phe Val Val Gly Val Thr Gly Asn Thr Met Thr Ile Leu Ile Ile Gln
    50                  55                  60

Tyr Phe Lys Asp Met Lys Thr Thr Thr Asn Leu Tyr Leu Ser Ser Met
65                  70                  75                  80

Ala Val Ser Asp Leu Val Ile Phe Leu Cys Leu Pro Phe Asp Leu Tyr
                85                  90                  95

Arg Leu Trp Lys Tyr Val Pro Trp Leu Phe Gly Glu Ala Val Cys Arg
            100                 105                 110

Leu Tyr His Tyr Ile Phe Glu Gly Cys Thr Ser Ala Thr Ile Leu His
        115                 120                 125

Ile Thr Ala Leu Ser Ile Glu Arg Tyr Leu Ala Ile Ser Phe Pro Leu
    130                 135                 140

Arg Ser Lys Val Met Val Thr Arg Arg Arg Val Gln Tyr Ile Ile Leu
145                 150                 155                 160

Ala Leu Trp Cys Phe Ala Leu Val Ser Ala Ala Pro Thr Leu Phe Leu
                165                 170                 175

Val Gly Val Glu Tyr Asp Asn Glu Thr His Pro Asp Tyr Asn Thr Gly
            180                 185                 190

Gln Cys Lys His Thr Gly Tyr Ala Ile Ser Ser Gly Gln Leu His Ile
        195                 200                 205
```

-continued

```
Met Ile Trp Val Ser Thr Thr Tyr Phe Phe Cys Pro Met Leu Cys Leu
    210                 215                 220

Leu Phe Leu Tyr Gly Ser Ile Gly Cys Lys Leu Trp Lys Ser Lys Asn
225                 230                 235                 240

Asp Leu Gln Gly Pro Cys Ala Leu Ala Arg Glu Arg Ser His Arg Gln
                245                 250                 255

Thr Val Lys Ile Leu Val Val Val Val Leu Ala Phe Ile Ile Cys Trp
            260                 265                 270

Leu Pro Tyr His Ile Gly Arg Asn Leu Phe Ala Gln Val Asp Asp Tyr
        275                 280                 285

Asp Thr Ala Met Leu Ser Gln Asn Phe Asn Met Ala Ser Met Val Leu
    290                 295                 300

Cys Tyr Leu Ser Ala Ser Ile Asn Pro Val Val Tyr Asn Leu Met Ser
305                 310                 315                 320

Arg Lys Tyr Arg Ala Ala Ala Lys Arg Leu Phe Leu Leu His Gln Arg
                325                 330                 335

Pro Lys Pro Ala His Arg Gly Gln Gly Gln Phe Cys Met Ile Gly His
            340                 345                 350

Ser Pro Thr Leu Asp Glu Ser Leu Thr Gly Val
        355                 360


<210> SEQ ID NO 8
<211> LENGTH: 27
<212> TYPE: DNA
<213> ORGANISM: Artificial Sequence
<220> FEATURE:
<223> OTHER INFORMATION: PCR Primer

<400> SEQUENCE: 8

ccatcctaat acgactcact atagggc                                          27


<210> SEQ ID NO 9
<211> LENGTH: 33
<212> TYPE: DNA
<213> ORGANISM: Artificial Sequence
<220> FEATURE:
<223> OTHER INFORMATION: PCR Primer

<400> SEQUENCE: 9

ttatcccatc gtcttcacgt tagcgcttgt ctc                                   33


<210> SEQ ID NO 10
<211> LENGTH: 30
<212> TYPE: DNA
<213> ORGANISM: Artificial Sequence
<220> FEATURE:
<223> OTHER INFORMATION: PCR Primer

<400> SEQUENCE: 10

ctgccctttc tgtgcctcag catcctctac                                       30


<210> SEQ ID NO 11
<211> LENGTH: 900
<212> TYPE: DNA
<213> ORGANISM: Homo sapiens

<400> SEQUENCE: 11

atgggcagcc cctggaacgg cagcgacggc cccgaggggg cgcgggagcc gccgtggccc      60

gcgctgccgc cttgcgacga gcgccgctgc tcgccctttc ccctgggggc gctggtgccg     120

gtgaccgctg tgtgcctgtg cctgttcgtc gtcggggtga gcggcaacgt ggtgaccgtg     180
```

-continued

```
atgctgatcg ggcgctaccg ggacatgcgg accaccacca acttgtacct gggcagcatg    240

gccgtgtccg acctactcat cctgctcggg ctgccgttcg acctgtaccg cctctggcgc    300

tcgcggccct gggtgttcgg gccgctgctc tgccgcctgt ccctctacgt gggcgagggc    360

tgcacctacg ccacgctgct gcacatgacc gcgctcagcg tcgagcgcta cctggccatc    420

tgccgcccgc tccgcgcccg cgtcttggtc acccggcgcc gcgtccgcgc gctcatcgct    480

gtgctctggg ccgtggcgct gctctctgcc ggtcccttct tgttcctggt gggcgtcgag    540

caggaccccg gcatctccgt agtcccgggc ctcaatggca ccgcgcggat cgcctcctcg    600

cctctcgcct cgtcgccgcc tctctggctc tcgcgggcgc caccgccgtc cccgccgtcg    660

gggcccgaga ccgcggaggc cgcggcgctg ttcagccgcg aatgccggcc gagccccgcg    720

cagctgggcg cgctgcgtgt catgctgtgg gtcaccaccg cctacttctt cctgcccttt    780

ctgtgcctca gcatcctcta cgggctcatc gggcgggagc tgtggagcag ccggcggccg    840

ctgcgaggcc cggccgcctc ggggcgggag agaggccacc ggcagaccgt ccgcgtcctg    900
```

<210> SEQ ID NO 12
<211> LENGTH: 300
<212> TYPE: PRT
<213> ORGANISM: Homo sapiens

<400> SEQUENCE: 12

```
Met Gly Ser Pro Trp Asn Gly Ser Asp Gly Pro Glu Gly Ala Arg Glu
 1               5                  10                  15

Pro Pro Trp Pro Ala Leu Pro Pro Cys Asp Glu Arg Arg Cys Ser Pro
            20                  25                  30

Phe Pro Leu Gly Ala Leu Val Pro Val Thr Ala Val Cys Leu Cys Leu
        35                  40                  45

Phe Val Val Gly Val Ser Gly Asn Val Val Thr Val Met Leu Ile Gly
    50                  55                  60

Arg Tyr Arg Asp Met Arg Thr Thr Thr Asn Leu Tyr Leu Gly Ser Met
65                  70                  75                  80

Ala Val Ser Asp Leu Leu Ile Leu Leu Gly Leu Pro Phe Asp Leu Tyr
                85                  90                  95

Arg Leu Trp Arg Ser Arg Pro Trp Val Phe Gly Pro Leu Leu Cys Arg
            100                 105                 110

Leu Ser Leu Tyr Val Gly Glu Gly Cys Thr Tyr Ala Thr Leu Leu His
        115                 120                 125

Met Thr Ala Leu Ser Val Glu Arg Tyr Leu Ala Ile Cys Arg Pro Leu
    130                 135                 140

Arg Ala Arg Val Leu Val Thr Arg Arg Arg Val Arg Ala Leu Ile Ala
145                 150                 155                 160

Val Leu Trp Ala Val Ala Leu Leu Ser Ala Gly Pro Phe Leu Phe Leu
                165                 170                 175

Val Gly Val Glu Gln Asp Pro Gly Ile Ser Val Val Pro Gly Leu Asn
            180                 185                 190

Gly Thr Ala Arg Ile Ala Ser Ser Pro Leu Ala Ser Ser Pro Pro Leu
        195                 200                 205

Trp Leu Ser Arg Ala Pro Pro Pro Ser Pro Pro Ser Gly Pro Glu Thr
    210                 215                 220

Ala Glu Ala Ala Ala Leu Phe Ser Arg Glu Cys Arg Pro Ser Pro Ala
225                 230                 235                 240

Gln Leu Gly Ala Leu Arg Val Met Leu Trp Val Thr Thr Ala Tyr Phe
                245                 250                 255
```

-continued

```
Phe Leu Pro Phe Leu Cys Leu Ser Ile Leu Tyr Gly Leu Ile Gly Arg
            260                 265                 270

Glu Leu Trp Ser Ser Arg Arg Pro Leu Arg Gly Pro Ala Ala Ser Gly
        275                 280                 285

Arg Glu Arg Gly His Arg Gln Thr Val Arg Val Leu
    290                 295                 300


<210> SEQ ID NO 13
<211> LENGTH: 154
<212> TYPE: DNA
<213> ORGANISM: Homo sapiens

<400> SEQUENCE: 13

cgtaagtgga gccgccgtgg ttccaaagac gcctgcctgc agtccgcccc gccggggacc      60

gcgcaaacgc tgggtcccct tcccctgctc gcccagctct gggcgccgct tccagctccc     120

tttcctattt cgattccagc ctccacccgc cggt                                 154


<210> SEQ ID NO 14
<211> LENGTH: 602
<212> TYPE: DNA
<213> ORGANISM: Homo sapiens

<400> SEQUENCE: 14

agctggtggt ggttctggca tttataattt gctggttgcc cttccacgtt ggcagaatca      60

tttacataaa cacggaagat tcgcggatga tgtacttctc tcagtacttt aacatcgtcg     120

ctctgcaact tttctatctg agcgcatcta tcaacccaat cctctacaac ctcatttcaa     180

agaagtacag agcggcggcc tttaaactgc tgctcgcaag gaagtccagg ccgagaggct     240

tccacagaag cagggacact gcgggggaag ttgcagggga cactggagga gacacggtgg     300

gctacaccga gacaagcgct aacgtgaaga cgatgggata acgtaagtgg agccgccgtg     360

gttccaaaga cgcctgcctg cagtccgccc cgccggggac cgcgcaaacg ctgggtcccc     420

ttcccctgct cgcccagctc tgggcgccgc ttccagctcc ctttcctatt tcgattccag     480

cctccacccg ccgtggtggt ggttctggca tttataattt gctggttgcc cttccacgtt     540

ggcagaatca tttacataaa cacggaagat tcgcggatga tgtacttctc tcagtacttt     600

aa                                                                    602


<210> SEQ ID NO 15
<211> LENGTH: 198
<212> TYPE: PRT
<213> ORGANISM: Homo sapiens

<400> SEQUENCE: 15

Leu Val Val Val Leu Ala Phe Ile Ile Cys Trp Leu Pro Phe His Val
 1               5                  10                  15

Gly Arg Ile Ile Tyr Ile Asn Thr Glu Asp Ser Arg Met Met Tyr Phe
            20                  25                  30

Ser Gln Tyr Phe Asn Ile Val Ala Leu Gln Leu Phe Tyr Leu Ser Ala
        35                  40                  45

Ser Ile Asn Pro Ile Leu Tyr Asn Leu Ile Ser Lys Lys Tyr Arg Ala
    50                  55                  60

Ala Ala Phe Lys Leu Leu Leu Ala Arg Lys Ser Arg Pro Arg Gly Phe
65                  70                  75                  80

His Arg Ser Arg Asp Thr Ala Gly Glu Val Ala Gly Asp Thr Gly Gly
                85                  90                  95
```

-continued

```
Asp Thr Val Gly Tyr Thr Glu Thr Ser Ala Asn Val Lys Thr Met Gly
            100                 105                 110

Arg Lys Trp Ser Arg Arg Gly Ser Lys Asp Ala Cys Leu Gln Ser Ala
        115                 120                 125

Pro Pro Gly Thr Ala Gln Thr Leu Gly Pro Leu Pro Leu Leu Ala Gln
    130                 135                 140

Leu Trp Ala Pro Leu Pro Ala Pro Phe Pro Ile Ser Ile Pro Ala Ser
145                 150                 155                 160

Thr Arg Arg Gly Gly Gly Ser Gly Ile Tyr Asn Leu Leu Val Ala Leu
                165                 170                 175

Pro Arg Trp Gln Asn His Leu His Lys His Gly Arg Phe Ala Asp Asp
            180                 185                 190

Val Leu Leu Ser Val Leu
        195
```

CLONING AND IDENTIFICATION OF THE MOTILIN RECEPTOR

FIELD OF THE INVENTION

The present invention is directed to a novel human DNA sequence encoding a motilin receptor, the receptor encoded by the DNA, and the uses thereof.

BACKGROUND OF THE INVENTION

Gastrointestinal (GI) motility is a coordinated neuromuscular process which transports nutrients through the digestive system. Impaired GI motility, can lead to irritable bowel syndrome, constipation and diabetic and post-surgical gastroporesis and is one of the largest health care burdens of industrialized nations. Motilin, a 22 amino acid prokinetic peptide is expressed throughout the gastrointestinal tract in a number of species including humans. Released from endochromafffin cells of the small intestine, motilin exerts a profound effect on gastric motility with the induction of interdigestive (phase III) antrum and duodenal contractions. The unrelated macrolide antibiotic erythromycin also possesses prokinetic properties mediated by its interaction with motilin receptors. These account for erythromycin's GI side-effects, including vomiting, nausea, diarrhea and abdominal muscular discomfort.

Motilin receptors have been detected in the GI tract and recently in the central nervous system, but their molecular structure has not been reported. Although motilin receptor characterization has been actively pursued in humans and other species since the isolation of motilin from porcine intestine in 1972, the receptor itself has not been isolated nor cloned.

Motilin is highly conserved across species and is synthesized as part of larger pre-prohormone. Mature 22 amino acid motilin is generated by removal of its secretory signal peptide and cleavage at the first C-terminally located dibasic prohormone convertase recognition site. Using radioligand binding, autoradiography and in vitro biossays, high affinity and low density, motilin receptors were detected in smooth muscle cells of the gastrointestinal tract of humans, cats and rabbits. Cerebellar brain receptors for motilin were also described supporting the notion that motilin may act in the central nervous system. Native motilin receptors appear to be coupled to G proteins and activate the phosphlipase C signal tranduction pathway resulting in $Ca^{2+}$ influx through L-type channels.

The development of safe and selective motilin receptor agonists is likely to aid the treatment of disorders resulting from impaired GI motility. Thus, it would be desirable to be able to isolate, and clone the motilin receptor, and to use this in assays for agonists and antagonists.

SUMMARY OF THE INVENTION

The present invention is directed to a novel G-protein coupled receptor (GPCR), designated as motilin receptor. Two spliced forms of the motilin receptor were identified: MTL-R1A, which encodes a functional seven-transmembrane domain form, and MTL-R1B, which encodes a truncated five-transmembrane domain form. Both forms make up embodiments of this invention.

Another aspect of this invention are nucleic acids which encode the motilin receptor, which are isolated, or free from associated nucleic acids.

Other aspects of this invention include assays for identifying motilin ligands which are agonists and antagonists of a motilin receptor comprising contacting a candidate ligand with a motilin receptor and determining if binding occurred.

Another aspect of this invention is a method for determining whether a ligand is capable of binding to a motilin receptor comprising:

(a) transfecting test cells with an expression vector encoding motilin receptor;

(b) exposing the test cells to the ligand;

(c) measuring the amount of binding of the ligand to the motilin receptor;

(d) comparing the amount of binding of the ligand to the motilin receptor in the test cells with the amount of binding of the ligand to control cells that have not been transfected with the motilin receptor where if the amount of binding of the ligand to the test cells is greater than the amount of binding of the ligand to the control cells, then the substance is capable of binding to motilin receptor.

BRIEF DESCRIPTION OF THE DRAWINGS

FIG. 1 shows the DNA sequence of motilin receptor gene including 5' untranslated region (SEQ. ID. NO.:1). Intronic sequences are shown in lower case type.

FIG. 2 shows the DNA sequence of motilin receptor spliced form A (MTL-R1A) (SEQ. ID. NO.:2).

FIG. 3 shows deduced amino acid sequence of MTL-R1A (SEQ. ID. NO.:3).

FIG. 4 shows the DNA sequence of motilin receptor spliced form B (MTL-R1B) (SEQ. ID. NO.:4).

FIG. 5 shows the deduced amino acid sequence of MTL-R1B (SEQ. ID. NO.:5).

FIGS. 6 A–C compare DNA (SEQ ID NOS: 2 and 4 respectively) and protein sequence for MTL-R1A (FM-1A) (SEQ ID NO: 3) and MTL-R1B (FM-1B)(SEQ ID NO: 5).

FIG. 7 shows the DNA sequence of puffer fish clone 75E7 (SEQ. ID. NO.:6).

FIG. 8 shows the deduced amino acid sequence of puffer fish clone 75E7 protein sequences (SEQ. ID. NO.:7).

FIG. 9 shows the comparison of human MTL-R1A (huMTLR)(SEQ ID NO: 3) and puffer fish clone 75E7 (pu75E7)(SEQ ID NO: 6) protein sequences.

Figure 10:
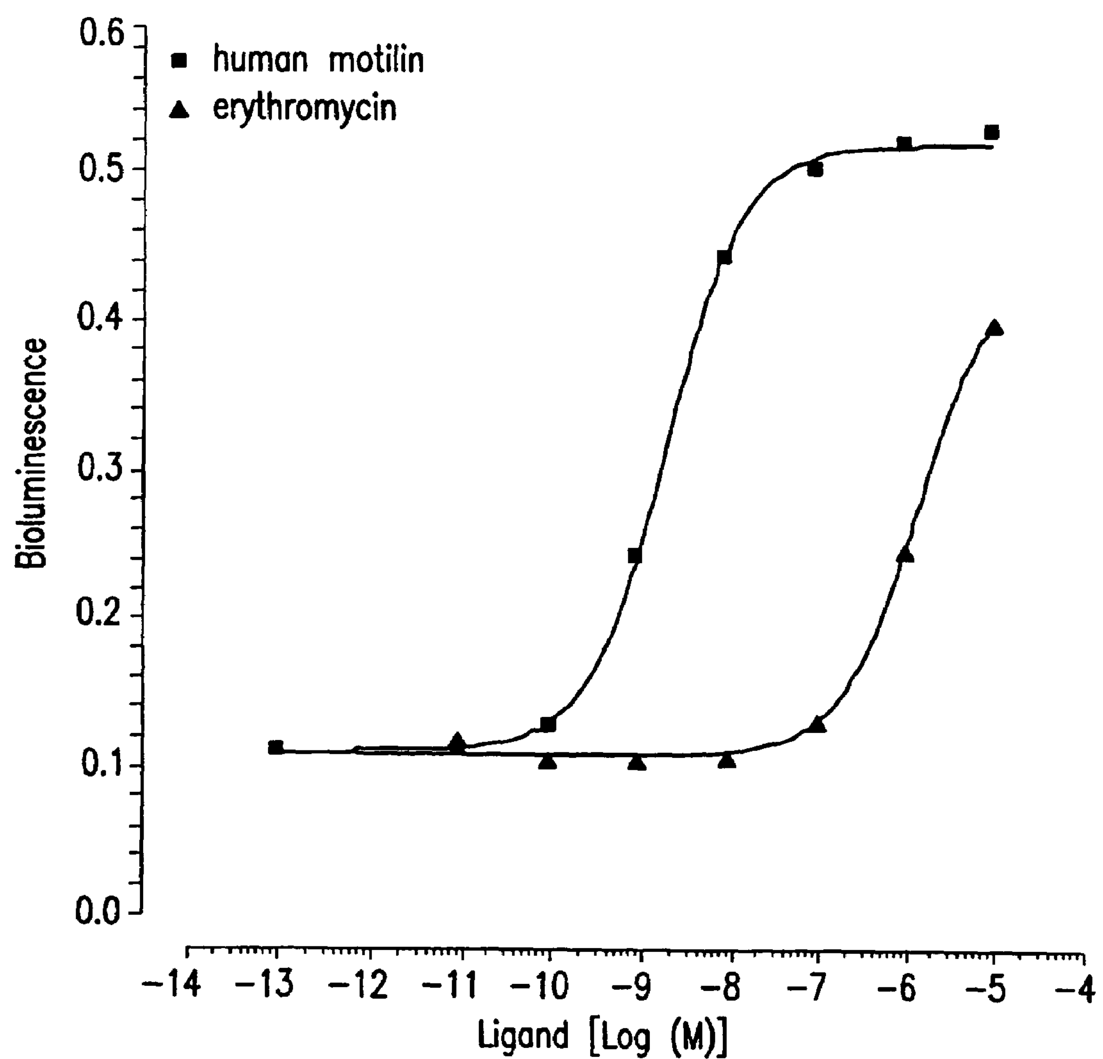
FIG. 10 is a graph illustrating the pharmacological characterization of the cloned MTL-R1A in the aequorin bioluminescence assay in HEK-293 cells.

As used throughout the specification and claims, the following definitions apply:

"Substantially free from other proteins" means at least 90%, preferably 95%, more preferably 99%, and even more preferably 99.9%, free of other proteins. Thus, for example, a MTL-R1 protein preparation that is substantially free from other proteins will contain, as a percent of its total protein, no more than 10%, preferably no more than 5%, more preferably no more than 1%, and even more preferably no more than 0.1%, of non- MTL-R1 proteins. Whether a given MTL-R1 protein preparation is substantially free from other proteins can be determined by such conventional techniques of assessing protein purity as, e.g., sodium dodecyl sulfate polyacrylamide gel electrophoresis (SDS-PAGE) combined with appropriate detection methods, e.g., silver staining or immunoblotting.

"Substantially free from other nucleic acids" means at least 90%, preferably 95%, more preferably 99%, and even more preferably 99.9%, free of other nucleic acids. Thus, for example, a MTL-R1 DNA preparation that is substantially free from other nucleic acids will contain, as a percent of its total nucleic acid, no more than 10%, preferably no more than 5%, more preferably no more than 1%, and even more preferably no more than 0.1%, of non- MTL-R1 nucleic acids. Whether a given MTL-R1 DNA preparation is substantially free from other nucleic acids can be determined by such conventional techniques of assessing nucleic acid purity as, e.g., agarose gel electrophoresis combined with appropriate staining methods, e.g., ethidium bromide staining, or by sequencing.

"Functional equivalent" means a receptor which does not have the exact same amino acid sequence of a naturally occurring motilin receptor, due to alternative splicing, deletions, mutations, or additions, but retains at least 1%, preferably 10%, and more preferably 25% of the biological activity of the naturally occurring receptor. Such derivatives will have a significant homology with a motilin receptor and can be detected by reduced stringency hybridization with a DNA sequence obtained from a motilin receptor. The nucleic acid encoding a functional equivalent has at least about 50% homology at the nucleotide level to a naturally occurring receptor nucleic acid.

"Ligand" means any molecule which binds to a motilin receptor of this invention. These ligands can have either agonist, partial agonist, partial antagonist or antagonist activity.

DETAILED DESCRIPTION OF THE INVENTION

The cloning of GPCR's related to the hypothalamic and pituitary receptor for the growth, hormone (GH) secretagogues (GHSs) which mediate sustained pulsatile GH release has been recently described. (McKee et. al., 1997 *Genomics* 46:426–434, which is hereby incorporated by reference). One of these clones, GPR38, possessed the most significant amino acid sequence identity to the human GHSR (52%) (rising to as high as 86% in transmembrane domains (TM). GPR38 was classified as an orphan GPCR (GPCRs for which a natural ligand has not been identified).

GPR38 was isolated from a human genomic DNA library and contained a single intron of approximately 1 kb, as shown in FIG. 1. cDNA clones were isolated to obtain the nucleotide sequence of correctly spliced GPR38 mRNA. Efforts to isolate cDNA clones by standard library screening proved unsuccessful.

A combination of RACE and RT-PCR techniques resulted in the identification of two spliced forms for GPR38. These two GPR38 cDNAs use distinct splice donor sites and a common acceptor site (perfect match to consensus exon-intron splice acceptor junction sequence [pyrimidine-rich stretch ag/TG]). GPR38-A mRNA (imperfect match to consensus donor sequence [TGC/gt]) encodes a polypeptide of 412 amino acids with seven alphahelical TM domains, the hallmark feature of GPC-Rs, whereas GPR38-B encodes a 363 amino acid polypeptide with five TM domains (perfect donor sequence [CCG/gt]). Northern blot analysis failed to reveal an expression profile for GPR38. However, when RNase protection was employed expression was demonstrated in stomach, thyroid and bone marrow.

It accordance with this invention, it has been found that GPR38 is the motilin receptor. Thus, this invention is directed to the human motilin receptor, its functional equivalents, motilin receptors from other species which can be isolated using fragments of the human motilin DNA as probes, and to splice varients of the motilin receptor.

The intact motilin receptor of this invention was found to have structural features which are typical of G-protein linked receptors, including seven transmembrane (TM) domains, three intra- and extracellular loops, and the GPCR protein signature sequence. The TM domains and GPCR protein signature sequence are noted in the protein sequences of the GPCR in FIGS. 6A–C.

A high-throughput assay was developed which measures $Ca^{2+}$realease with the bioluminescent $Ca^{2+}$sensitive-aequorin reporter protein (capable of measuring ligand-induced IP3-coupled mobilization of intracellular calcium and concomitant calcium-induced aequorin bioluminescence). Expression of cloned GPR38-A in cell membranes was confirmed using epitope-tagged protein which revealed a single protein species with a molecular weight of approximately 45,000 daltons containing an open reading frame encoding 412 amino acids (SEQ. ID. NO.:3). The DNA and deduced amino acid sequence are given in SEQ. ID. NO.:2 and SEQ. ID. NO.:3, respectively.

A broad set of peptide and non-peptide molecules were tested at a single concentration in transiently transfected HEK-293/aeq17 cells (100 nM peptide, 10 μM non-peptide). Significant bioluminescent responses were recorded for the peptide motilin and the non-peptide macrolide erythromycin, which was reported to be a competitive agonist at motilin receptors. Full dose-response curves confirmed this observation.

Nucleotide sequence analysis revealed two splice forms of human motilin receptor both of which make up further aspects of this invention. The first (MTL-R1A) encodes a seven transmembrane domain receptor. The full length open reading frame appears to contain 412 amino acids. The second splice form (MTL-R1B) diverges in its nucleotide sequence from MTL-R1A just before the predicted amino acid of the sixth transmembrane domain (TM6).

In the MTL-R1B, TM5 is truncated and fused to a contiguous reading frame of about 86 amino acids, followed by a translation stop codon. The DNA and amino acids sequences encoding MTL-R1A and MTL-R1B are given in FIGS. 2–5.

A further aspect of this invention is a related motilin receptor gene, evident in the teleost puffer fish *Spheroides nephelus*. Screening of a puffer fish genomic library identified a single clone (75E7) containing an open reading frame of 363 amino acids (approximately 54% identical at the protein level) which contains a similar exon-intron structure to GPR38. Analysis of clone 75E7 shows an amino acid sequence to contain 363 amino acids with a molecular weight of approximately 41,323 daltons. (FIG. 8). DNA sequence of puffer fish clone 75E7 is given in SEQ. ID. NO.:6, and a comparison of human MTL-R1A and puffer fish clone 75E7 protein sequences is given in FIG. 9.

Another aspect of this invention relates to vectors which comprise nucleic acids encoding a motilin receptor or a functional equivalent. These vectors may be comprised of DNA or RNA; for most cloning purposes DNA vectors are preferred. Typical vectors include plasmids, modified viruses, bacteriophage and cosmids, yeast artificial chromosomes and other forms of episomal or integrated DNA that encode a motilin receptor. It is well within the skill of the ordinary artisan to determine an appropriate vector for a particular gene transfer or other use.

A further aspect of this invention are host cells which are transformed with a gene which encodes a motilin receptor or a functional equivalent. The host cell may or may not naturally express a motilin receptor on the cell membrane. Preferrably, once transformed, the host cells are able to express the motilin receptor or a functional equivalent on the cell membrane. Depending on the host cell, it may be desirable to adapt the DNA so that particular codons are used in order to optimize expression. Such adaptations are known in the art, and these nucleic acids are also included within the scope of this invention. Generally mammalian cell lines, such as HEK-293, COS, CHO, HeLa, NS/), CV-1, GC, GH3 or VERO cells are preferred host cells, but other cells and cell lines such as *Xenopus oocytes* or insect cells, may also be used.

Human embryonic kidney (HEK 293) cells and Chinese hamster ovary (CHO) cells are particularly suitable for expression of motilin receptor proteins because these cells express a large number of G-proteins. Thus, it is likely that at least one of these G-proteins will be able to functionally couple the signal generated by interaction of motilin receptors and their ligands, thus transmitting this signal to downstream effectors, eventually resulting in a measurable change in some assayable component, e.g., cAMP level, expression of a reporter gene, hydrolysis of inositol lipids, or intracellular $Ca^{2+}$ levels.

A variety of mammalian expression vectors can be used to express recombinant motilin in mammalian cells. Commercially available mammalian expression vectors which are suitable include, but are not limited to, pCR2.2 (Invitrogen), pMClneo (Stratagene), pSG5 (Stratagene), pcDNAI and pcDNAIamp, pcDNA3, pcDNA3.1, pCR3.1 (Invitrogen), EBO-pSV2-neo (ATCC 37593), pBPV-1(8–2) (ATCC 37110), pdBPV-MMTneo (342–12) (ATCC 37224), pRSVgpt (ATCC 37199), pRSVneo (ATCC 37198), and pSV2-dhfr (ATCC 37146). Following expression in recombinant cells, motilin receptors can be purified by conventional techniques to a level that is substantially free from other proteins.

The specificity of binding of compounds showing affinity for motilin receptors is shown by measuring the affinity of the compounds for recombinant cells expressing the cloned receptor or for membranes from these cells. Expression of the cloned receptor and screening for compounds that bind to motilin receptors or that inhibit the binding of a known, radiolabeled ligand of motilin receptors to these cells, or membranes prepared from these cells, provides an effective method for the rapid selection of compounds with high affinity for a motilin receptor. Such ligands need not necessarily be radiolabeled but can also be nonisotopic compounds that can be used to displace bound radiolabeled compounds or that can be used as activators in functional assays. Compounds identified by the above method are likely to be agonists or antagonists of motilin receptors and may be peptides, proteins, or non-proteinaceous organic molecules.

Such molecules are useful in treating a variety of gastric conditions, including gastric motility disorders (intrinsic myopathies or neuropathy), functional defects, disorders which are secondary to neurologic disorders including spinal cord transections, amyloidosis, collagen vascular disease (e.g. scleroderma), paraneoplastic syndromes, radiation-induced dysmotility, diabetes, infections, stress-related motiliy disorders, psychgenic/functional disorders, other drugs which affect motility (e.g. beta andrenergic drugs which may delay gastric emptying, cholinergic agents or opiates, or serotonin receptor antagonists), gastroparesis (diabetic or post-surgical), gastro-esophageal reflux disease, constipation, chronic idiopathis pseudo-obstruction and acute fecal impaction, postoperative ileus, gallstones, infantile collic, preparation for colonoscopy and endoscopy, duodenal intubation, irritable bowel syndrome, non-ulcer dyspepsion, non-cardiac chest pain and diarrhea.

Figure 11:
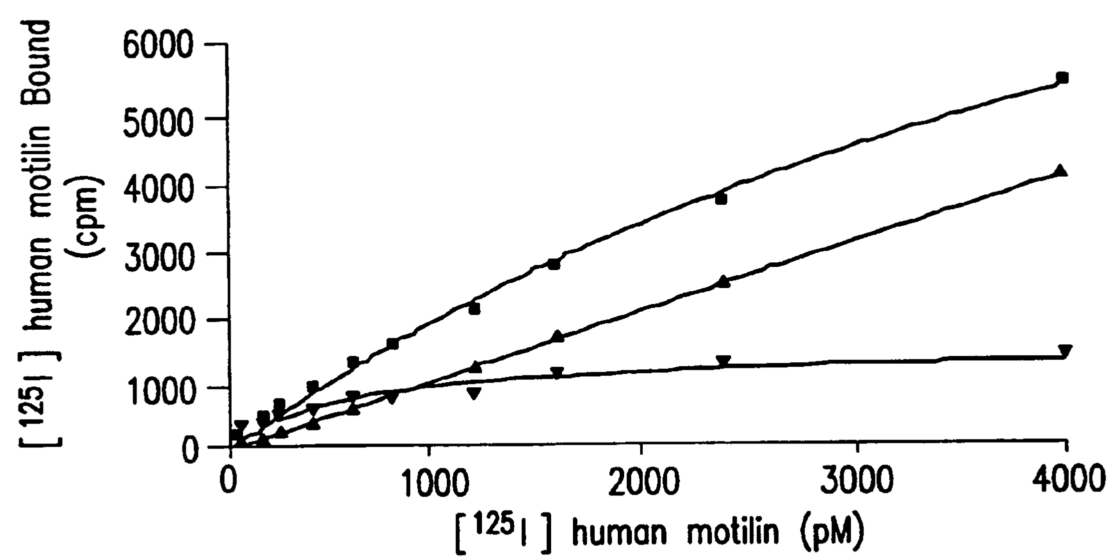
FIG. 11 is a graph illustrating the pharmacological characterization of the cloned MTL-R1A in the $[^{125}I]$-$Tyr^7$-human motilin binding assay.

The pharmacological characterization of the cloned MTL-R1A in the aequorin bioluminescence assay in HEK-293 cells is shown in FIG. 10 and in the $[^{125}I]$-$Tyr^7$-human motilin binding assay (FIG. 11). Motilin at concentrations as high as 10 μM gave no bioluminescent response above background levels in cells that were not transfected with the MTL-R1A cDNA expression vector. Similarly, non-transfected cells did not show appreciable binding of $[^{125}I]$-$Tyr^7$-human motilin.

The rank order of potency for motilin, motilin peptide fragments and non-peptide molecules is consistent with experiments performed on native motilin receptors, from stomach or intestinal tissues.

Due to the high degree of homology to GPCRs, the motilin receptor of this invention is believed to function similarly to GPCRs and have similar biological activity. They are useful in understanding the biological and physiological pathways involved in gastrointestinal motility. They may be also used to scan for motilin agonists and antagonists; as in particular to test the specificity of identified ligands.

The following, non-limiting Examples are presented to better illustrate the invention.

EXAMPLE 1

Sequence Comparison of MTL-R1 (GPR38) to Human GHS-R, Puffer Fish 75E7 and Identification of Alternatively Spliced Forms Inspection of the MTL-1 genomic DNA sequence revealed two potential mRNA splice sites corresponding to consensus boundaries for exon/intron junctions. An imperfect donor site (TGC/gt) was found at nucleotides 1929–31 (FIG. 1), a perfect donor site (CCG/gt) was found at nucleotides 2080–82, and a single perfect splice acceptor site (sequence [pyrimidine-rich stretch ag/TG]) was observed at nucleotides 2729–32. To determine which splice forms exist naturally, RACE,(rapid amplification of cDNA ends) was performed on thyroid poly (A)+ mRNA and RT-PCR (reverse transcriptase polymerase chain reaction) was conducted on HEK-293/aeq17 cells transfected with the MTL-1 genomic DNA construct. Directional RACE reactions were conducted on thyroid poly (A)+ mRNA that had previously been shown by RNase protection assay to contain transcripts for MTL-1R. Primer AP1 5'-CCA TCC TAA TAC GAC TCA CTA TAG GGC-3' (SEQ. ID. NO.:8) corresponds to the 5' end of the coding region including the presumptive Met initiation codon located within the cloning vector. 5'RACE1 corresponds to the 3' end of the MTL-1R coding region including the translation termination codon TAA. 5' RACE1: 5'-TTA TCC CAT CGT CTT CAC GTT AGC GCT TGT CTC-3' (SEQ. ID. NO.:9).

RACE reactions were carried out on 1 μg of thyroid poly (A)+ mRNA using the Marathon cDNA amplification/advantage PCR kit as per the manufacturer's instructions (Clontech) using the following Touchdown PCR amplification conditions: 94° C. for 1 min., 5 cycles of 94° C. for 30 sec. and 72° C. for 4 min.; 5 cycles of 94° C. for 30 sec. and 70° C. for 4 min.; 25 cycles of 94° C. for 20 sec and 68° C. for 4 min. An approximately 1.4 kb amplified product was identified which hybridized with a $^{32}P$-labeled probe derived from the TM 2–4 region (3F/4R probe) of the MTL-R. This product was subcloned into PCR-Script vector (Invitrogen) and sequenced.

As diagrammed in FIGS. 6A–C, DNA sequence analysis revealed two distinct sequences corresponding to alternative use of two splice donor sequences and a common splice acceptor sequence. These results were confirmed by transfecting the MTL-1 genomic construct containing the complete ORF interrupted by a single intron of approximately 0.7 kb into HEK-293/aeq17 cells. mRNA was the isolated (Poly (A) Pure Kit, Ambion) and shown by Northern blot analysis using the 3F/4R probe to give two hybridizing bands: 2.4 kb containing the unspliced intron and approximately 1.4 kb encoding spliced forms. RT-PCR was then performed (Superscript 2 One-Step Kit, Life Technologies) on MTL-1 mRNA from transfected HEK-293/aeq17 cells using the forward primer 5' RACE1 and reverse primer 3' RACE2 (TM5 region): 5'-CTG CCC MTT CTG TGC CTC AGC ATC CTC TAC-3' (SEQ. ID. NO.:10)

An approximately 500 bp product was cloned (TA vector pCR2.2, Invitrogen), sequenced and shown to be a mixture of both splice forms. Assembly of the complete ORF for MTL-1A without intronic sequence was performed by ligation of an exon 1 fragment (Not I digestion of a MTL-1 plasmid containing the intron in pCDNA-3) to pCDNA-3.1 containing a Not 1/EcoR 1 exon 2 fragment.

To document protein expression, an MTL-1A plasmid encoding a amino-terminal FLAG epitope was constructed by ligation of a Pme 1 fragment from the MTL-1A/pcDNA-1.1 vector into the EcoRV site of pFLAG/CMV-2 vector (Kodak Imaging Systems). Following transfection of this plasmid into HEK-293/aeq17 cells, a protein of the expected size (approximately 48 kDa) was detected in crude cell membranes by immunoblot analysis.

EXAMPLE 2

Identification of Ligand Specific to Motilin Receptor

To identify a ligand for this orphan GPCR and to determine whether the full length, 7 TM domain GPR38-A is a functional GPCR, a high-throughput assay was developed which measures $Ca^{2+}$ release with the bioluminescent $Ca^{2+}$ sensitive aequorin reporter protein (capable of measuring ligand-induced $IP_3$-coupled mobilization of intracellular calcium and concomitant calcium-induced aequorin bioluminescence). Expression of GPR38-A in cell membranes was confirmed using epitope-tagged protein which revealed a single protein species with a molecular weight of approximately 45,000 daltons.

A broad set of peptide and non-peptide molecules was tested at a single concentration in transiently transfected HEK-293/aeq17 cells (100 nM peptide, 10 μM non-peptide). Significant bioluminescent responses (>4-fold over background) were recorded for the peptide motilin and the non-peptide macrolide erythromycin, which was reported to be a competitive agonist at motilin receptors. Full dose-response curves confirmed this observation. The half-maximal effective concentration ($EC_{50}$) for human/porcine motilin was 2.1+/−0.5 nM motilin whereas erythromycin was considerably less potent (2000+/−210 nM; as expected from studies performed on native motilin receptors).

The signal tranduction pathway for the cloned GPR38-A motilin receptor (MTL-R1A) is through activation of phospholipase C, which has been reported for native motilin receptors. Direct radioligand binding studies with [$^{125}$I] human motilin on cell membranes prepared from transfected cells show that MTL-R1A confers high affinity and specific binding ($K_d$=0.1 nM; $B_{max}$=240 fmol/mg protein) which are strongly G protein coupled (>80% inhibition of binding with 100 nM GTPγS).

EXAMPLE 3

Functional Activation of the MTL-1A Receptor

The aequorin bioluminescence assay is a reliable test for identifying G protein-coupled receptors which couple through the Gα protein subunit family consisting of $G_q$ and $G_{11}$ which leads to the activation of phospholipase C, mobilization of intracellular calcium and activation of protein kinase C. Measurement of MTL-1A expression in the aequorin-expressing stable reporter cell line 293-AEQ17 (Button, D. et. al., 1993 *Cell Calcium* 14: p. 663–671.) was performed using a Luminoskan RT luminometer (Labsystems Inc., Gaithersburg, Md.).

293-AEQ17 cells (8×105 cells plated 18 hrs. before transfection in a T75 flask) were transfected with 22 μg of human MTL-R1A plasmid DNA: 264 μg lipofectamine. Following approximately 40 hours of expression the apo-aequorin in the cells was charged for 4 hours with coelenterazine (10 μM) under reducing conditions (300 μM reduced glutathione) in ECB buffer (140 mM NaCl, 20 mM KCl, 20 mM HEPES—NaOH [pH=7.4], 5 mM glucose, 1 mM $MgCl_2$, 1 mM $CaCl_2$, 0.1 mg/ml bovine serum albumin). The cells were harvested, washed once in ECB medium and resuspended to 500,000 cells/ml. 100 μl of cell suspension (corresponding to $5\times10^4$ cells) was then injected into the test plate, and the integrated light emission was recorded over 30 seconds, in 0.5 second units. 20 μL of lysis buffer (0.1% final Triton X-100 concentration) was then injected and the integrated light emission recorded over 10 seconds, in 0.5 second units. The "fractional response" values for each well were calculated by taking the ratio of the integrated response to the initial challenge to the total integrated luminescence including the Triton X-100 lysis response.

EXAMPLE 4

Binding of [$^{125}$I] Human Motilin to Crude Membranes from HEK-293 Cells Transfected with the MTL-R1A cDNA The binding of [$^{125}$I] human motilin to crude membranes prepared from HEK-293/aeq17 cell transfectants was performed as follows. Crude cell membranes were prepared on ice, 48 hrs. post-transfection. Each T-75 flask was washed twice with 10 ml of PBS, once with 1 ml homogenization buffer (50 mM Tris-HCl [pH 7.4], 10 mM $MgCl_2$. 10 ml of homogenization buffer was added to each flask, cells were removed by scraping and then homogenized using a Polytron device (Brinkmann, Syosset, N.Y.; 3 bursts of 10 sec. at setting 4). The homogenate was centrifuged for 20 min. at 11,000×g at 0° C. and the resulting crude membrane pellet (chiefly containing cell membranes and nuclei) was resuspended in homogenization buffer supplemented with 1.5% BSA (0.5 ml T75 flask) and kept on ice.

Binding reactions were performed at 20° C. for 1 hr. in a total volume of 0.5 ml containing: 0.1 ml of membrane suspension (approximately 1 μg protein), 10 μl of $^{125}$I-human motilin, 10 μl of competing drug and 380–390 μl of homogenization buffer. Bound radioligand was separated by rapid vacuum filtration (Brandel 48-well cell harvester) through GF/C filters pretreated for 1 hr. with 0.5% polyethylenimine. After application of the membrane suspension to the filter, the filters were washed 3 times with 3 ml each of ice-cold 50 mM Tris-HCl [pH 7.4], 10 mM $MgCl_2$, and the bound radioactivity on the filters was quantitated by gamma counting. Specific binding (>90% of total) is defined as the difference between total binding and non-specific binding conducted in the presence of 100 nM unlabeled human motilin. Competition binding data were analyzed by a non-linear curve-fitting program (Prism V, version 2.0; GraphPad Software, San Diego, Calif.). Results shown are the means (+/−SEM) of triplicate determinations Human motilin was radiolabeled with $^{125}$I at $^{7}$Tyr to a specific activity of approximately 2000 Ci/mmol (Woods Assay, Portland, Oreg.).

Structure-function analysis suggest that the motilin peptide minimally contains an N-terminal region (amino acids 1–7) essential for activity, linked to a C-terminal alpha helical domain which stabilizes the N-terminal active site region activity. The rank, order of potency of several motilin peptide analogs in the MTL1-A functional and binding assays correlates with their reported potency measured by in vitro contractility assays (Table 1) performed on native motilin receptors in intestinal tissue. These results are summarized in Table 1 below.

| | Cloned MTL-1A Receptor (human) | |
|---|---|---|
| Ligand | Aequorin Assay ($EC_{50}$ nM) | [$^{125}$I] hmotilin binding ($IC_{50}$, nM) |
| human motilin (MTL) | 2.1 | 0.5 |
| erythromycin | 2000 | 427 |
| roxithromycin | 1950 | 613 |
| metoclopramide | >10,000 | >10,000 |
| cisapride | >10,000 | >10,000 |
| canine motilin | 4.4 | 0.2 |
| Leu$^{13}$ MTL | 3.9 | 0.2 |
| 1-11 MTL | 138 | 127 |
| 1-12 MTL | 72 | 14 |
| 1-13 MTL | 3.8 | 0.9 |
| 1-19 MTL | 4.1 | 0.3 |
| 10-22 MTL | >10,000 | 1100 |

The unrelated prokinetic agents metoclopromide and cisapride which have affinity for dopamine and/or 5-HT receptors were inactive, even at high (10 μM) doses.

EXAMPLE 5

Southern Blot Analysis

A genomic Southern blot (EcoRI and BamH1-digested DNA, 10 μg/lane) was hybridized with the ORF of MTL-1A. Post-hybridizational washing stringencies were at 55° C. 4X SSPE after which the filters were dried and exposed to X-ray film for 5 days at −70° C. Lambda Hind III DNA markers were (in kb), 23.1, 9.4, 6.6, 4.4, 2.3, 2.1. Southern blot analysis conducted in a variety of mammalian and non-mammalian species revealed a simple hybridization pattern consistent with a single, conserved gene encoding MTL-1A.

EXAMPLE 6

Puffer Fish Clone 75E7

Screening of a puffer fish genomic library identified a single clone (75E7) containing an open reading frame of 363 amino acids with approximately 54% protein sequence identity to the human MTL-R1A In addition, 75E7 has a similar intron-exon structure to the human MTL-R1A. 75E7 may be the ortholog of the human MTL-R1A.

EXAMPLE 7

Expression of the MTL-R1A Gene

Transcripts of MTL-1A were detected by RNase Protection Assay (RPA). Synthesis of high-specific activity radio-labeled antisense probes and the RPA was conducted using a kit (MAXIscript and HybSpeed RPA kits; Ambion, Austin, Tex.) essentially as described by the manufacturer. The anti-sense cRNA MTL-1A probe was synthesized from a cDNA template encompassing nt 1234 to 1516 of the human MTL-1A inserted behind the T7 promoter in pLitmus 28 (New England Biolabs, Beverly, Mass.). Digestion of the construct with Stu I generated a cRNA transcript approximately 340 nt in size with approximately 60 nt of vector sequence. Input poly $A^+$ mRNA (Clontech, Palo Alto, Calif.) was 5 g for the MTL-1A probe and 0.1 μg for a control human actin probe. Precipitated fragments were subjected to slab-gel electrophoresis (42 cm×32 cm×0.4 mm) in 5% acrylamide/Tris-borate-EDTA buffer containing 8 M urea. The gels were fixed, dried and autoradiographed on film (X-Omat; Kodak, Rochester, N.Y.) for 1–3 days (MTL-1A) or 2 hrs. (actin).

The distribution profile of MTL-1A mRNA was examined in a panel of GI and non-GI human tissues. MTL-1A mRNA could be detected in whole stomach (most prominently), thyroid, and bone marrow but was absent from several brain regions and other non-CNS tissues.

What is claimed is:

1. An isolated polypeptide consisting of the amino acid sequence set forth in SEQ ID NO: 3 which functions as a receptor for motilin.

2. An isolated polypeptide consisting of the amino acid sequence encoded by the nucleotide sequence set forth in SEQ ID NO: 2 which functions as a receptor for motilin.

3. A method for determining whether a test compound is capable of agonizing or antagonizing motilin binding comprising:

(a) transfecting indicator cells with an expression vector comprising a nucleic acid encoding a polypeptide consisting of the amino acid sequence set forth in SEQ ID NO: 3 which functions as a receptor for motilin;

(b) exposing the indicator cells to the test compound in the presence of detectably labeled motilin;

(c) measuring the amount of motilin binding to the indicator cells;

(d) comparing the amount of motilin binding to the indicator cells with the amount of motilin binding to cells exposed to the detectably-labeled motilin in the absence of a test compound; wherein if the amount of motilin binding to the indicator cells in the presence of the test compound differs from the amount of motilin binding in the absence of the test compound, then the test compound is capable of agonizing or antagonizing motilin binding.

4. An expression vector comprising a polynucleotide sequence which encodes a polypeptide according to claim 1.

5. A recombinant host cell transfected with a vector according to claim 4.

* * * * *